US008252907B2

(12) United States Patent
Krah, III et al.

(10) Patent No.: US 8,252,907 B2
(45) Date of Patent: *Aug. 28, 2012

(54) METHODS AND COMPOSITIONS FOR INHIBITING BINDING OF IGE TO A HIGH AFFINITY RECEPTOR

(75) Inventors: Eugene Regis Krah, III, Freeport, ME (US); Robert Lawton, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,986

(22) Filed: Mar. 7, 2011
(Under 37 CFR 1.47)

(65) Prior Publication Data
US 2011/0158981 A1 Jun. 30, 2011

Related U.S. Application Data

(60) Division of application No. 12/117,872, filed on May 9, 2008, now Pat. No. 7,931,898, which is a division of application No. 10/325,375, filed on Dec. 20, 2002, now Pat. No. 7,393,529, which is a continuation-in-part of application No. 09/592,998, filed on Jun. 12, 2000, now Pat. No. 6,504,013, application No. 13/041,986, which is a continuation-in-part of application No. 09/281,761, filed on Mar. 30, 1999, now abandoned, which is a continuation-in-part of application No. 09/058,332, filed on Apr. 9, 1998, now abandoned, application No. 13/041,986, which is a continuation-in-part of application No. 09/281,760, filed on Mar. 30, 1999, now Pat. No. 6,734,287, which is a continuation-in-part of application No. 09/058,331, filed on Apr. 9, 1998, now abandoned.

(60) Provisional application No. 60/179,629, filed on Feb. 1, 2000.

(51) Int. Cl.
*C07K 16/00* (2006.01)

(52) U.S. Cl. ............... 530/387.9; 530/387.3; 530/388.1; 530/388.25; 424/133.1; 424/139.1; 424/141.1; 424/145.1

(58) Field of Classification Search .......................... None
See application file for complete search history.

(56) References Cited

U.S. PATENT DOCUMENTS

| 5,180,805 | A | 1/1993 | Gould |
| 5,321,123 | A | 6/1994 | Griffin |
| 5,422,258 | A | 6/1995 | Chang |
| 5,475,096 | A | 12/1995 | Gold |
| 5,514,776 | A | 5/1996 | Chang |
| 5,543,144 | A | 8/1996 | Chang |
| 5,595,877 | A | 1/1997 | Gold |
| 5,629,415 | A | 5/1997 | Hollis |
| 5,653,980 | A | 8/1997 | Hellman |
| 5,660,985 | A | 8/1997 | Pieken |
| 5,670,626 | A | 9/1997 | Chang |
| 5,756,291 | A | 5/1998 | Griffin |
| 5,840,867 | A | 11/1998 | Toole |
| 5,861,254 | A | 1/1999 | Schneider |
| 5,866,136 | A | 2/1999 | Ramshaw |
| 5,994,511 | A * | 11/1999 | Lowman et al. ........... 530/387.3 |
| 6,025,164 | A | 2/2000 | Bolin |
| 6,110,466 | A | 8/2000 | Lomonossoff |
| 6,180,348 | B1 | 1/2001 | Li |
| 6,504,013 | B1 * | 1/2003 | Lawton et al. ............. 530/387.3 |
| 6,811,782 | B1 | 11/2004 | Wang |
| 7,931,898 | B2 | 4/2011 | Lawton |

FOREIGN PATENT DOCUMENTS

| EP | 0419858 | 4/1991 |
| EP | 095573111 | 11/1999 |
| JP | 0383579 | 4/1991 |
| JP | 03123489 | 5/1991 |
| JP | 0440894 | 12/1992 |
| WO | 89/06138 | 7/1989 |
| WO | WO 9304173 A1 * | 3/1993 |
| WO | 95/31728 | 11/1995 |
| WO | 97/33616 | 9/1997 |
| WO | 99/31262 | 6/1999 |
| WO | 99/49890 | 10/1999 |
| WO | 99/54452 | 10/1999 |
| WO | 00/53722 | 9/2000 |
| WO | 00/58349 | 10/2000 |
| WO | 00/58365 | 10/2000 |
| WO | 01/02924 | 1/2001 |
| WO | 01/57090 | 9/2001 |

OTHER PUBLICATIONS

Shields et al., Int Arch Allergy Immunol. May-Jun. 1995;107(1-3):308-12.*
Zheng et al., Biochem Biophys Res Commun. Oct. 31, 2008;375(4):619-22.*
Ishida, et al., "The nucleotide sequence of the mouse immunoglobulin epsilon gene: comparison with the human epsilon gene sequence", The EMBO Journal, vol. 1, No. 9, pp. 1117-1123 (1982).
Posnett, et al., "A Novel Method for Producing Anti-Peptide Angitobides", The Journal of Biological Chemistry, vol. 263, No. 4, pp. 1719-1825 (1988).
Auriault, et al., "Epitopic Characterization and Vaccinal Potential of Peptides Derived from a Major Antigen of Schistosoma Mansoin (Sm28 GST)", Peptide Research, vol. 4, No. 1, pp. 6-11 (1991).
Patel, et al., "Sequence of the dog immunoglobulin alpha and epsilon constant region genes", Immunogenetics, 41:282-286 (1995).
Tam, et al., "Multiple Antigen Peptide", Journal of Immunological Methods, 124, pp. 53-61 (1989).
Hill, et al., "Quantification of serum total IgE concentration in dogs by use of an enzyme-linked immunosorbent assay containing monoclonal murine anti-canine IgE", Am. J. Vet. Res., vol. 55, No. 7, pp. 944-948 (1994).

(Continued)

*Primary Examiner* — Michael Szperka
(74) *Attorney, Agent, or Firm* — McDonnell Boehnen Hulbert & Berghoff LLP

(57) ABSTRACT

The invention provides methods and compositions for inhibiting binding of IgE to a high affinity receptor. The methods and compositions are useful in the treatment of allergic diseases and allergy symptoms in mammals.

9 Claims, 14 Drawing Sheets

OTHER PUBLICATIONS

Konieczny, et al., "The major dog allergents, Can f1 and Can f2, are salivary lipoalin proteins: cloning and immunological characterization of the recombinant forms", Immunology, 92, pp. 577-586 (1997).

Colman, "Effects of amino acid sequence changes on antibody-antigen interactions:", Research in Immunology, 145 (1):33-36 (1994).

Tam, "Synethic peptide vaccine design: Synthesis and properties of a high-density multiple antgenic peptide systems", Proc. Natl. Acad. Sci. USA, vol. 65, pp. 5409-5413 (1988).

Blind, et al., "Cytoplasmic RNA modulators of an inside-out signal-transduction cascade", Proc. Natl. Acad. Sci. USA, vol. 96, pp. 3606-3610 (1999).

Conry, et al.,"Phase I Trial of a Recombinant Vaccinia Virus Encoding Carcinoembryonic Antigen in Metastatic Adenocarcinoma: Comparison of Intradermal versus Subcutaneous Administration", Clinical Cancer Research, vol. 5, pp. 2330-2337 (1999).

Jameson, et al., "The antigenic index: a novel algorithm for predicting antigenic determinants", CABIOS, vol. 4, No. 1, pp. 181-186 (1988).

Akhtar, et al., "Cellular uptake and intracellular fate of antisense oligonucleotides", Trends in Cell Biology, vol. 2, pp. 139-145 (1992).

Maurer, et al., "Lipid-based systems for the intracellular delivery of genetic drugs", Molecular Membrane Biology, vol. 16, pp. 129-140 (1999).

Hofland, et al., "Formulation and Delivery of Nucleic Acids", Handb. Exp. Pharamcol. Chapter 8, pp. 165-192 (1999).

Conrad, et al., "In Vitro Selection of Nucleic Acid Aptamers that Bind Proteins", Methods of Enzymology, vol. 267, pp. 336-367 (1996).

Kohler, et al., "Continuous cultures of fused cells screting antibody of predefined specificity", Nature, vol. 256, pp. 495-497 (1975).

Neuberger, et al., "A hapten-specific chimaeric IgE antibody with human physiological effector function", Nature, vol. 314, pp. 268-270 (1985).

Ellington, et al., "In vitro selection of RNA molecules that bind specific ligands", Nature, vol. 346, pp. 818-822 (1990).

Bock, et al., "Selection of single-stranded DNA molecules that bind and inhibit human thrombin", Nature, vol. 355, pp. 564-566 (1992).

Bowie, et al., "Deciphering the Message in Protein Sequences: Tolerance to Amino Acid Substitutions", Science, vol. 247, pp. 1306-1310 (1990).

*Cunningham, et al., "High-Resolution Epitope Mapping of hGH-Receptor Interactions by Alanine-Screening Mutagenesis", Reports, pp. 1081-1085 (1989).

Tuerk, et al., "Systematic Evolution of Ligands by Exponential Enrichment: RNA Ligands to Bacteriophage T4 DNA Polymerase", Science, pp. 505-510 (1990).

Osbourne, et al., "Aptamers as therapeutic and diagnostic reagents: problems and prospects", Current Opinion in Chemical Biology, pp. 5-9 (1997).

Lee, et al., "Modified Liposome Formulations for Cytosolic Delivery of Macromolecules", American Chemical Society, pp. 184-192 (2000).

Wilson, et al., "In vitro Selection of Functional Nucleic Acids", Annu. Rev. Biochem., 66:611-674 (1999).

Aldin, et al., "Antisense oligonucleotides to the GluR2 AMPA receptor subunit modify excitatory synaptic transmission in vivo", Elsevier, 55, pp. 151-164 (1998).

Chun, et al., "Effect of infusion of vasoactive intestinal peptide (VIP)-antisense oligodeoxynucleotide into the third cerebral ventricle above the hypothalamic suprachiasmatic nucleus on the hyperglycemia caused by intracranial injection of 2-deoxy-D-glucose in rates", Elsevier, 257, pp. 135-138 (1998).

Ghimikar, et al., Chemokine inhibition in rat stab wound brain injury using antisense oligodeoxynucleotides, Elsevier, 247, pp. 21-24 (1998).

Gold, "Axonal Regeneration of Sensory Nerves is Delayed by Continuous Intrathecal Infusion of Nerve Growth Factor", Neuroscience, vol. 76, No. 4, pp. 1153-1158 (1997).

Dryden, et al., "The lack of specificity of neuropeptide Y (NPY) antisense oligodeoxynucleotides administered intracerebroventricularly in inhibiting food intake and NPY gene expression in the rat hypothalamus", Journal of Endocrinology, 157, pp. 16-175 (1998).

Broaddus, et al., "Distribution and stability of antisense phosphorothioate oligonucleotides in rodent brain following direct intraparenchymal controlled-rate infusion", Neurosurg. Focus, 3(5):1-14 (1997).

Ngo, et al., "Computational Complexity, Protein Structure Prediction, and the Levinthal Paradox", the Protein Folding Problem and Tertiary Structure Prediction, pp. 433-506 (1994).

Supplemental Partial European Search Report for corresponding European application No. 0318142436.6 dated Nov. 7, 2007.

Sutton, et al., "Inhibition of IgE-receptor interactions", British Medical Bulletin 56 (No. 4):1004-1018 (2000).

Chang, "The pharmacological basis of anti-IgE therapy", Nature Biotechnology, vol. 18, p. 157-162 (2000).

Babu, et al., "Anti-IgE Treatment: An Update", Allergy, 56:1121-1126 (2001).

* cited by examiner

Figure 1

15A2 Binding Phage

Sequence of Displayed Peptide

| Library | | | | | | | | | | | | | | | Isolate |
|---|---|---|---|---|---|---|---|---|---|---|---|---|---|---|---|
| PhDc7c | SEQ ID NO:15 | | | | C | S | N | P | H | V | T | H | C | | M13 1&9 |
| PhDc7c | SEQ ID NO:16 | | | | C | S | H | P | H | L | T | H | C | | M13 7 |
| PhDc7c | SEQ ID NO:17 | | | | C | S | N | P | H | I | T | Q | C | | M13 10 |
| PhDc7c | SEQ ID NO:18 | | | | C | M | N | P | H | I | T | H | C | | M13 14 |
| PhDc7c | SEQ ID NO:19 | | | | C | T | N | P | H | N | P | Y | C | | M13 2&8 |
| PhDc7c | SEQ ID NO:20 | | | | C | P | N | P | H | N | P | Y | C | | M13 3&5 |
| PhD12 | SEQ ID NO:13 | V | T | L | C | P | N | P | H | I | P | M | C | | M13 48 |
| PhDc7c | SEQ ID NO:11 | | | | | C | H | P | H | L | P | K | S | C | M13 4&12 |
| PhDc7c | SEQ ID NO:12 | | | | | C | H | P | H | L | P | K | R | C | M13 6 |
| | SEQ ID NO:2 | Y | C | R | V | T | H | P | H | L | P | K | D | I | V R S I — Canine IgE |

**Peptide inhibition of
15A2/IgE interaction.**

**Peptide inhibition of
15A2/IgE interaction.**

Figure 4

IgE Alignment 15A2 Epitope                                                      Species

Y   C   R   V   T   H   P   H   L   P   K   D   I   V   R   S   I        Canine SEQ ID NO:2

Q   C   R   V   T   H   P   H   L   P   R   A   L   M   R   S   T       Human SEQ ID NO:3

Q   C   R   V   T   H   P   H   L   P   R   A   L   V   R   S   T       Green Monkey
                                                                                                     SEQ ID NO:4

Q   C   K   V   T   H   P   D   L   P   L   V   I   V   R   S   I        Cat  SEQ ID NO:5

Y   C   N   V   T   H   P   D   L   P   K   P   I   L   R   S   I        Swine  SEQ ID NO:6

Q   C   I   V   D   H   P   D   F   P   *   *   I   V   R   S   I        Mouse SEQ ID NO:7

K   C   T   V   S   H   P   D   L   P   R   E   V   V   R   S   I        Horse  SEQ ID NO:8

\* Denotes a deletion.

ized sequence listing text file, which was electronically submitted along with this document. The text file is named "01_672_EDIV2_SL.txt" is 6.06 kilobytes, and was created on Mar. 7, 2011.

METHODS AND COMPOSITIONS FOR INHIBITING BINDING OF IGE TO A HIGH AFFINITY RECEPTOR

PRIORITY INFORMATION

This application is divisional of U.S. Ser. No. 12/117,872, filed on May 9, 2008 (now allowed), which is a divisional of U.S. Ser. No. 10/325,375, filed on Dec. 20, 2002 (now U.S. Pat. No. 7,393,529), which is a continuation-in-part of U.S. application Ser. No. 09/592,998, filed Jun. 12, 2000 (now U.S. Pat. No. 6,504,013), which claims the benefit of U.S. Application Ser. No. 60/179,629, filed Feb. 1, 2000.

This application is also a continuation-in-part of U.S. application Ser. No. 09/281,761, filed Mar. 30, 1999 (now abandoned), which is a continuation-in-part of U.S. application Ser. No. 09/058,332, filed Apr. 9, 1998 (now abandoned).

This application is also a continuation-in-part of U.S. application Ser. No. 09/281,760, filed Mar. 30, 1999 (now U.S. Pat. No. 6,734,287), which is a continuation-in-part of U.S. application Ser. No. 09/058,331, filed Apr. 9, 1998, now abandoned. All of these applications are incorporated by reference herein in their entirety.

SEQUENCE LISTING

This document incorporates by reference an electronic sequence listing text file, which was electronically submitted along with this document. The text file is named "01_672_EDIV2_SL.txt" is 6.06 kilobytes, and was created on Mar. 7, 2011.

BACKGROUND OF THE INVENTION

Excessive production of Immunoglobulin E (IgE) is the hallmark of allergic response to allergens. IgE exerts its primary role through cross-linking of the high-affinity IgE receptor ($Fc_\epsilon RI$) on mast cells and basophils, resulting in degranulation with the release of histamines and other molecules that produce symptoms associated with allergy.

In contrast, another membrane protein on B lymphocytes (also expressed on macrophages and platelets), CD23 ($Fc_\epsilon RII$), the low-affinity receptor for IgE, plays an important role in decreasing IgE-associated allergic response through regulation of IgE production.

Therefore, therapeutic substances that inhibit binding of free IgE to high affinity receptors on mast cells and basophils can be useful to reduce allergic symptoms. It would also be advantageous if such substances also did not substantially interfere with IgE binding to the low affinity receptors on B lymphocytes so as not to increase IgE production.

SUMMARY OF THE INVENTION

The present invention provides compositions and methods of inhibiting allergic symptoms by inhibition of binding of free IgE to high affinity receptors on mast cells and basophils. More specifically, it was discovered that a monoclonal antibody, designated 15A.2, has the ability to block that portion of IgE that would otherwise bind to high affinity receptors on mast cells and basophils. Further investigation lead to the discovery of particular amino acid sequences (polypeptides) that correspond to the epitope on IgE that achieves the aforementioned blocking effect. Therefore, the present invention not only relates to the 15A.2 antibody and polypeptide epitopes on IgE that are specific for 15A.2, but also to other antibodies, polypeptides, and nucleic acids that would compete with 15A.2 for binding the disclosed epitope on IgE. It is believed that the disclosed antibody and polypeptides also do not substantially interfere with IgE binding to the low affinity receptors on B lymphocytes so as not to increase IgE production. In addition, it is believed that the disclosed antibody, epitope bound by the antibody and polypeptides are useful across many species.

One embodiment of the invention provides an isolated polypeptide consisting essentially of an amino acid sequence of Xaa Cys Xaa Val Xaa His Pro Xaa Xaa Pro Xaa Xaa Xaa Xaa Arg Ser Xaa (SEQ ID NO:1). The polypeptide can be derived from a mammal. The amino acid in position 1 can be Gln, Tyr, or Lys, the amino acid in position 3 can be Arg, Lys, Asn, Ile, or Thr, the amino acid in position 5 can be Thr, Asp, or Ser, the amino acid in position 8 can be Asp or His, the amino acid in position 9 can be Leu or Phe, the amino acid in position 11 can be Lys, Arg, Leu or absent, the amino acid in position 12 can be Ala, Asp, Val, Pro, Glu or absent, the amino acid in position 13 can be Ile, Leu, or absent, the amino acid in position 14 can be Val, Met, Leu, Val, or Trp, and the amino acid in position 17 can be Ile or Thr. Alternatively, the amino acid in position 1 can be Gln, the amino acid in position 3 can be Arg or Xaa, the amino acid in position 5 can be Thr, the amino acid in position 8 can be Asp, the amino acid in position 9 can be Leu, the amino acid in position 11 can be Lys or Arg, the amino acid in position 12 can be Ala or Xaa, the amino acid in position 13 can be Ile, the amino acid in position 14 can be Val, the amino acid in position 17 can be Ile.

An amino acid sequence can be selected from the group consisting of:

```
                                               (SEQ ID NO: 2)
(a) Tyr Cys Arg Val Thr His Pro His Leu Pro Lys
    Asp Ile Val Arg Ser Ile;

(SEQ ID NO: 3)
(b) Gln Cys Arg Val Thr His Pro His Leu Pro Arg
    Ala Leu Met Arg Ser Thr;

(SEQ ID NO: 4)
(c) Gln Cys Arg Val Thr His Pro His Leu Pro Arg
    Ala Leu Val Arg Ser Thr;

(SEQ ID NO: 5)
(d) Gln Cys Lys Val Thr His Pro Asp Leu Pro Leu
    Val Ile Val Arg Ser Ile;

(SEQ ID NO: 6)
(e) Tyr Cys Asn Val Thr His Pro Asp Leu Pro Lys
    Pro Ile Leu Arg Ser Ile;

(SEQ ID NO: 7)
(f) Gln Cys Ile Val Asp His Pro Asp Phe Pro Ile
    Val Arg Ser Ile;
    and (SEQ ID NO: 8)
(g) Lys Cys Thr Val Ser His Pro Asp Leu Pro Arg
    Glu Val Val Arg Ser Ile.
```

Another embodiment of the invention provides an isolated polypeptide comprising an amino acid sequence of Xaa Cys Xaa Val Xaa His Pro Xaa Xaa Pro Xaa Xaa Xaa Xaa Arg Ser Xaa (SEQ ID NO:1), except SEQ ID NO:2, SEQ ID NO:3, SEQ. ID NO:4, SEQ. ID NO:5, SEQ ID NO:6, SEQ ID NO:7 and SEQ ID NO:8. The amino acid in position 1 can be Gln, Tyr, or Lys, the amino acid in position 3 can be Arg, Lys, Asn, Ile, or Thr, wherein the amino acid in position 5 can be Thr, Asp, or Ser, the amino acid in position 8 can be Asp or His, the amino acid in position 9 can be Leu or Phe, the amino acid in position 11 can be Lys, Arg, Leu or absent, the amino acid in position 12 can be Ala, Asp, Val, Pro, Glu or absent, the amino acid in position 13 can be Ile, Leu, or absent, the amino acid in position 14 can be Val, Met, Leu, Val, or Trp, and the amino acid in position 17 can be Ile or Thr. Alternatively, the amino acid in position 1 can be Gln, the amino acid in position 3 can be Arg or Xaa, the amino acid in position 5 can be Thr, the amino acid in position 8 can be Asp, the amino acid in position 9 can be Leu, the amino acid in position 11 can be Lys or Arg, the amino acid in position 12 can be Ala or Xaa, the amino acid in position 13 can be Ile, the amino acid in position 14 can be Val, the amino acid in position 17 can be Ile.

Still another embodiment of the invention provides a polypeptide fragment consisting essentially of about 9, 10, 11, 12, 13, 14, 15, 16, or 17 amino acids of SEQ ID NO:1.

Yet another embodiment of the invention provides an isolated polypeptide consisting essentially of an amino acid sequence of: Cys Xaa Xaa Pro His Xaa Xaa Xaa Cys (SEQ ID NO:9). The polypeptide can be derived from a mammal. The amino acid in position number 2 can be Ser, Met, Thr, or Pro, the amino acid in position number 3 can be Asn or His, the amino acid in position number 6 can be Val, Leu, Ile, or Asn, the amino acid in position number 7 can be Thr or Pro, the amino acid in position number 8 can be His, Gln, Tyr, or Met. Alternatively, the amino acid in position number 2 can be Ser or Pro, the amino acid in position number 3 can be Asn, the amino acid in position 6 can be Ile or Asn, the amino acid in position number 7 can be Thr or Pro, and the amino acid in position 8 can be His or Tyr.

Even another embodiment of the invention provides an isolated polypeptide comprising an amino acid sequence selected from the group consisting of:

```
                                        (SEQ ID NO: 10)
(a) Cys His Pro His Leu Pro Lys Xaa Cys;

(SEQ ID NO: 11)
(b) Cys His Pro His Leu Pro Lys Ser Cys;

(SEQ ID NO: 12)
(c) Cys His Pro His Leu Pro Lys Arg Cys;
    and (SEQ ID NO: 13)
(d) Val Thr Leu Cys Pro Asn Pro His Ile
    Pro Met Cys.
```

Another embodiment of the invention provides an isolated polynucleotide encoding an isolated polypeptide consisting essentially of an amino acid sequence of Xaa Cys Xaa Val Xaa His Pro Xaa Xaa Pro Xaa Xaa Xaa Xaa Arg Ser Xaa (SEQ ID NO:1) and/or an isolated polypeptide consisting essentially of an amino acid sequence of: Cys Xaa Xaa Pro His Xaa Xaa Xaa Cys (SEQ ID NO:9).

Yet another embodiment of the invention provides an isolated polynucleotide comprising an expression control sequence operably linked to a polynucleotide encoding SEQ ID NO:1 or SEQ ID NO:9 or both SEQ ID NO:1 and SEQ ID NO:9. The polynucleotide can be present in an expression vector. The expression vector can be present in a host cell.

Still another embodiment of the invention provides an antibody, antibody fragment, or single-chain antibody that binds specifically to an isolated polypeptide consisting essentially of an amino acid sequence of Xaa Cys Xaa Val Xaa His Pro Xaa Xaa Pro Xaa Xaa Xaa Xaa Arg Ser Xaa (SEQ ID NO:1) and/or an isolated polypeptide consisting essentially of an amino acid sequence of: Cys Xaa Xaa Pro His Xaa Xaa Xaa Cys (SEQ ID NO:9).

Even another embodiment of the invention provides an antibody, antibody fragment, or single-chain antibody that binds specifically to a polypeptide comprising SEQ ID NO:1, SEQ ID NO:9 or both SEQ ID NO:1 and SEQ ID NO:1 and SEQ ID NO:9.

Another embodiment of the invention provides a method of preventing an IgE molecule from binding to a high affinity receptor comprising contacting the IgE molecule with a molecule that specifically binds to a portion of the IgE molecule comprising SEQ ID NO:1, SEQ ID NO:9, or both SEQ ID NO:1 and SEQ ID NO:1 and SEQ ID NO:9, wherein binding of the IgE molecule to the high affinity receptor is prevented. The molecule can be an antibody, antibody fragment, single-chain antibody, or apatmer. The contacting can occur in a mammalian subject.

Yet another embodiment of the invention provides a composition for use in treatment or prevention of allergy symptoms in a mammalian subject, which comprises an immunologically effective amount of a polypeptide shown in SEQ ID NO:1 or SEQ ID NO:9 or both SEQ ID NO:1 and SEQ ID NO:9 and one or more pharmaceutically acceptable carriers. The composition can further comprise an adjuvant. An immunologically effective amount of the composition can be administered to a mammalian subject as a method for treatment or prevention of one or more allergy symptoms. The composition can be administered in association with an adjuvant.

Still another embodiment of the invention provides a composition for use in treatment or prevention of one or more allergy symptoms comprising an immunologically effective amount of an antibody, antibody fragment, or single-chain antibody that binds specifically to a polypeptide comprising SEQ ID NO:1, SEQ ID NO:9 or both SEQ ID NO:1 and SEQ ID NO:9 and one or more pharmaceutically acceptable carriers. An immunologically effective amount of the composition can be administered to a mammalian subject as a method for treatment or prevention of one or more allergy symptoms.

Even another embodiment of the invention provides a composition for use in the treatment or prevention or one or more allergy symptoms comprising an immunologically effective amount of a polynucleotide that encodes one or more polypeptides shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or fragments thereof and one or more pharmaceutically acceptable carriers. An immunologically effective amount of the composition can be administered to a mammalian subject as a method for treatment or prevention of one or more allergy symptoms.

Another embodiment of the invention provides an antibody, antibody fragment, or single-chain antibody that competes with monoclonal antibody 15A.2 for binding to an IgE molecule. The IgE molecule can be a mammalian IgE molecule.

Even another embodiment of the invention provides an antibody, antibody fragment, or single-chain antibody that competes with monoclonal antibody 15A.2 for binding to an IgE molecule. The binding of the antibody, antibody fragment or single-chain antibody or the monoclonal antibody 15A.2 to the IgE molecule inhibits binding of the IgE molecule to a high affinity receptor. The IgE molecule can be a mammalian IgE molecule.

Yet another embodiment of the invention provides a first antibody, antibody fragment, or single-chain antibody that competes with a second antibody, antibody fragment, or single-chain antibody that binds specifically to a polypeptide comprising an amino acid sequence of Xaa Cys Xaa Val Xaa His Pro Xaa Xaa Pro Xaa Xaa Xaa Xaa Arg Ser Xaa (SEQ ID NO:1) or Cys Xaa Xaa Pro His Xaa Xaa Xaa Cys (SEQ ID NO:9) for binding to an IgE molecule. The binding of the first or second antibody, antibody fragment, or single-chain antibody to the IgE molecule inhibits binding of the IgE molecule to a high affinity receptor. The IgE molecule can be a mammalian IgE molecule.

Still another embodiment of the invention provides a polypeptide that competes with monoclonal antibody 15A.2 for binding to an IgE molecule. The IgE molecule can be a mammalian IgE molecule.

Another embodiment of the invention provides a polypeptide or polynucleotide that competes with monoclonal antibody 15A.2 for binding to an IgE molecule. The binding of the polypeptide, polynucleotide, or the monoclonal antibody 15A.2 to the IgE molecule inhibits binding of the IgE molecule to a high affinity receptor. The IgE molecule can be a mammalian IgE molecule.

Yet another embodiment of the invention provides a polypeptide that competes with an antibody, antibody fragment, or single-chain antibody that binds specifically to a polypeptide comprising an amino acid sequence of Xaa Cys Xaa Val Xaa His Pro Xaa Xaa Pro Xaa Xaa Xaa Xaa Arg Ser Xaa (SEQ ID NO:1) or Cys Xaa Xaa Pro His Xaa Xaa Xaa Cys (SEQ ID NO:9 for binding to an IgE molecule. The binding of the polypeptide or antibody, antibody fragment, or single-chain antibody to the IgE molecule inhibits binding of the IgE molecule to a high affinity receptor. The IgE molecule can be a mammalian IgE molecule.

BRIEF DESCRIPTION OF THE DRAWINGS

FIG. 1 shows phage displayed peptide sequences that specifically bind monoclonal antibody 15A.2.

FIG. 3B is identical to FIG. 3A, except that the scale of the X axis has been expanded. For FIG. 3A-B the X axis is μg peptide/ml and the Y axis is optical density.

FIG. 4 shows mammalian IgE alignment with the 15A.2 epitope.

DETAILED DESCRIPTION OF THE INVENTION

Polypeptides of the Invention

Figure 2:
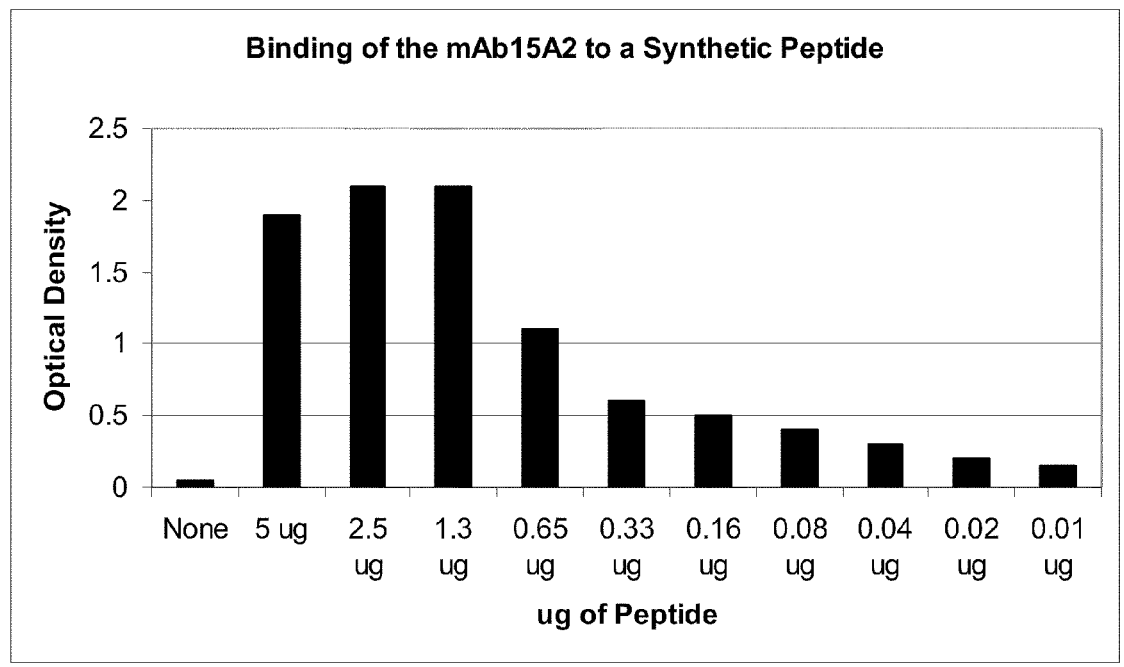
FIG. 2 shows binding of 15A.2 monoclonal antibody to a synthetic peptide.

An isolated polypeptide of the invention can comprise or consist essentially of an amino acid sequence of Xaa Cys Xaa Val Xaa His Pro Xaa Xaa Pro Xaa Xaa Xaa Xaa Arg Ser Xaa (SEQ ID NO:1). Xaa stands for any amino acid and in certain, noted instances, an absent amino acid (i.e., the Xaa at positions 11, 12, and/or 13 can be an absent amino acid). An absent amino acid means that no amino acid occurs at the specified position.

In one embodiment of invention, the amino acid in position 1 of SEQ ID NO:1 is Gln, Tyr, or Lys, the amino acid in position 3 is Arg, Lys, Asn, Ile, or Thr, the amino acid in position 5 is Thr, Asp, or Ser, the amino acid in position 8 is Asp or His, the amino acid in position 9 is Leu or Phe, the amino acid in position 11 is Lys, Arg, Leu or absent, the amino acid in position 12 is Ala, Asp, Val, Pro, Glu or absent, the amino acid in position 13 is Ile, Leu, or absent, the amino acid in position 14 is Val, Met, Leu, Val, or Trp, and the amino acid in position 17 is Ile or Thr. Additionally, the amino acid in position 1 of SEQ ID NO:1 is Gln, the amino acid in position 3 is Arg or Xaa, the amino acid in position 5 is Thr, the amino acid in position 8 is Asp, the amino acid in position 9 is Leu, the amino acid in position 11 is Lys or Arg, the amino acid in position 12 is Ala or Xaa, the amino acid in position 13 is Ile, the amino acid in position 14 is Val, and the amino acid in position 17 is Ile. In one embodiment of the invention a polypeptide has an amino acid sequence of:

```
                                          (SEQ ID NO: 2)
(a) Tyr Cys Arg Val Thr His Pro His Leu Pro Lys
    Asp Ile Val Arg Ser Ile;

(SEQ ID NO: 3)
(b) Gln Cys Arg Val Thr His Pro His Leu Pro Arg
    Ala Leu Met Arg Ser Thr;

(SEQ ID NO: 4)
(c) Gln Cys Arg Val Thr His Pro His Leu Pro Arg
    Ala Leu Val Arg Ser Thr;

(SEQ ID NO: 5)
(d) Gln Cys Lys Val Thr His Pro Asp Leu Pro Leu
    Val Ile Val Arg Ser Ile;

(SEQ ID NO: 6)
(e) Tyr Cys Asn Val Thr His Pro Asp Leu Pro Lys
    Pro Ile Leu Arg Ser Ile;

(SEQ ID NO: 7)
(f) Gln Cys Ile Val Asp His Pro Asp Phe Pro Ile
    Val Arg Ser Ile;
    and (SEQ ID NO: 8)
(g) Arg Cys Thr Val Ser His Pro Asp Leu Pro Arg
    Glu Trp Arg Ser Ile.
    See FIG 4.
```

In one embodiment of the invention an isolated polypeptide comprises or consists essentially of an amino acid sequence of Xaa Cys Xaa Val Xaa His Pro Xaa Xaa Pro Xaa Xaa Xaa Xaa Arg Ser Xaa (SEQ ID NO:1), except for SEQ ID NO:2, SEQ ID NO:3, SEQ. ID NO:4, SEQ. ID NO:5, SEQ ID NO:6, SEQ ID NO:7 and SEQ ID NO:8 (that is SEQ ID NOs:2-8 are not included in SEQ ID NO:1 in this embodiment).

The amino acid in position 1 of SEQ ID NO:1 can be Gln, Tyr, or Lys, the amino acid in position 3 can be Arg, Lys, Asn, Ile, or Thr, the amino acid in position 5 can be Thr, Asp, or Ser, the amino acid in position 8 can be Asp or His, the amino acid in position 9 can be Leu or Phe, the amino acid in position 11 can be Lys, Arg, Leu or absent, the amino acid in position 12 can be Ala, Asp, Val, Pro, Glu or absent, the amino acid in position 13 can be Ile, Leu, or absent, the amino acid in position 14 can be Val, Met, Leu, Val, or Trp, and the amino acid in position 17 can be Ile or Thr.

The amino acid in position 1 of SEQ ID NO:1 can be Gln, the amino acid in position 3 can be Arg or Xaa, the amino acid in position 5 can be Thr, the amino acid in position 8 can be Asp, the amino acid in position 9 can be Leu, the amino acid in position 11 can be Lys or Arg, the amino acid in position 12 can be Ala or Xaa, the amino acid in position 13 can be Ile, the amino acid in position 14 can be Val, the amino acid in position 17 can be Ile.

In one embodiment of the invention, an isolated polypeptide comprises or consists essentially of an amino acid sequence of: Cys Xaa Xaa Pro His Xaa Xaa Xaa Cys (SEQ ID NO:9).

The amino acid in position 2 of SEQ ID NO:9 can be Ser, Met, Thr, or Pro, the amino acid in position number 3 can be Asn or His, the amino acid in position number 6 can be Val, Leu, Ile, or Asn, the amino acid in position number 7 can be Thr or Pro, the amino acid in position number 8 can be His, Gln, Tyr, or Met.

The amino acid in position 2 of SEQ ID NO:9 can be Ser or Pro, the amino acid in position number 3 can be Asn, the amino acid in position 6 can be Ile or Asn, the amino acid in position number 7 can be Thr or Pro, and the amino acid in position 8 can be His or Tyr.

The invention also comprises or consists essentially of an amino acid sequence selected from the group consisting of:

```
                                          (SEQ ID NO: 10)
(a) Cys His Pro His Leu Pro Lys Xaa Cys;

(SEQ ID NO: 11)
(b) Cys His Pro His Leu Pro Lys Ser Cys;

(SEQ ID NO: 12)
(c) Cys His Pro His Leu Pro Lys Arg Cys;
    and (SEQ ID NO: 13)
(d) Val Thr Leu Cys Pro Asn Pro His Ile
    Pro Met Cys.
```

The basic and novel characteristics of polypeptides of the invention that consist essentially of SEQ ID NOs:1-13 are that they consist essentially of the sequences shown in SEQ ID NOs:1-13 and that they specifically bind to an antibody, antibody fragment, or single-chain antibody of the invention.

In one embodiment of the invention, a polypeptide or fragment thereof is substantially pure. Substantially pure means that a polypeptide of the invention is substantially free from other biological molecules. A substantially pure polypeptide is at least 75%, 80%, 90%, 95%, 97%, 99% or 100% pure by dry weight. Purity can be measured by a method such as column chromatography, polyacrylamide gel electrophoresis, or HPLC analysis.

The invention also includes functionally active variants of polypeptides shown in, for example, SEQ ID NOs:2-8 and 10-13. Functionally active variants of polypeptides shown in SEQ ID NOs: 2-8 and 10-13 retain the consensus sequences shown in SEQ ID NO:1 or SEQ ID NO:9 and yet can comprise amino acid substitutions or deletions at the Xaa residues of the consensus sequences. In one embodiment, the polypeptide includes an amino acid sequence at least about 60% identical to a sequence shown as SEQ ID NO:2-8 and 10-13, or a fragment thereof. Preferably, the polypeptide is at least 55%, 60%, 65%, 70%, 75%, 80%, 85%, 90%, 95%, 98%, 99% or more identical to SEQ ID NOs:2-8 and 10-13, encompasses consensus sequences as shown in SEQ ID NO:1 and/or SEQ ID NO:9, and specifically binds to an antibody of the invention. Polypeptides of the invention also specifically bind to an antibody, such as a monoclonal antibody, that is raised to a polypeptide shown in SEQ ID NO:1, SEQ ID NO:9, both SEQ ID NOs:1 and 9, or SEQ ID NOs:2-8 and 10-13.

Polypeptides of the invention specifically bind to an antibody of the invention. In this context "specifically binds" means that the polypeptide recognizes and binds to an antibody of the invention with greater affinity than to other, non-specific molecules. For example, an antibody raised against an antigen (polypeptide) to which it binds more efficiently than to a non-specific protein can be described as specifically binding to the antigen. Binding specifically can be tested using, for example, an enzyme-linked immunosorbant assay (ELISA), a radioimmunoassay (RIA), or a western blot assay using methodology well known in the art.

A polypeptide is a functionally active variant if it reacts substantially the same as a polypeptide shown in SEQ ID NOs:2-8 and 10-13 in an assay such as an immunohistochemical assay, an ELISA, an RIA, or a western blot assay, e.g. has 90-110% of the specific binding activity of the original polypeptide. In one embodiment, the assay is a competition assay wherein the functionally active variant polypeptide is capable of reducing binding of a polypeptide shown in SEQ ID NOs:2-8 and 10-13 to a corresponding antibody, antibody fragment, or single-chain antibody by about 80, 95, 99, or 100%.

Functionally active variants can also comprise "polypeptide fragments" of the invention. Polypeptide fragments comprise or consist essentially of about 9, 10, 11, 12, 13, 14, 15, 16, or 17 amino acids of SEQ ID NO:1-13.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means amino acid sequence (or nucleic acid sequence) similarity and has an art recognized meaning Sequences with identity share identical or similar amino acids (or nucleic acids). Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

Functionally active variants of SEQ ID NOs:2-8 and 10-13 retain substantially the same functional activity of the original polypeptide or fragment. Naturally occurring functionally active variants such as allelic variants and species variants and non-naturally occurring functionally active variants are included in the invention and can be produced by, for example, mutagenesis techniques or by direct synthesis.

A functionally active variant differs by about, for example, 1, 2, 3, 4, 5, 6, 7, 8, 9, or 10 amino acid residues from a polypeptide shown in SEQ ID NOs:2-8 and 10-13 or a fragment thereof, and yet retains a consensus sequence SEQ ID NO:1 or SEQ ID NO:9. Where this comparison requires alignment the sequences are aligned for maximum homology. The site of variation can occur anywhere in the polypeptide, as long as activity substantially similar to a polypeptide shown in SEQ ID NOs:2-8 and 10-13 is maintained and the SEQ ID NO:1 or SEQ ID NO:9 consensus sequences are maintained within the functionally active variant. That is, a functionally active variant will comprise SEQ ID NO:1 or SEQ ID NO:9.

Guidance concerning how to make phenotypically silent amino acid substitutions is provided in Bowie et al., *Science*, 247:1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. See e.g., FIG. 4 and SEQ ID NO:1 and 9. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific binding activity of the polypeptide.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., *Science*, 244:1081-1085 (1989)). The resulting variant molecules can then be tested for specific binding to antibodies of the invention.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a polypeptide functionally active variant to a polypeptide by replacing an amino acid that does not influence the function of a polypeptide can be accomplished by one skilled in the art.

In one embodiment of the invention, a polypeptide of the invention is derived from a mammal, such as a human, a non-human primate, a cat, a dog, a horse, a mouse, a rat, or a swine. A polypeptide of the invention can be isolated from cells or tissue sources using standard protein purification techniques. Polypeptides of the invention can also be synthesized chemically or produced by recombinant DNA techniques. For example, a polypeptide of the invention can be synthesized using conventional peptide synthesizers. Additionally, a polynucleotide encoding a polypeptide of the invention can be introduced into an expression vector that can be expressed in a suitable expression system using techniques well known in the art. A variety of bacterial, yeast, plant, mammalian, and insect expression systems are available in the art and any such expression system can be used. Optionally, a polynucleotide encoding a polypeptide of the invention can be translated in a cell-free translation system.

A functionally active variant polypeptide can also be isolated using a hybridization technique. Briefly, DNA having a high homology to the whole or part of a nucleic acid sequence encoding SEQ ID NOs:2-8 and 10-13 is used to prepare a functionally active polypeptide. Therefore, a polypeptide of the invention also includes polypeptides that are functionally equivalent to a SEQ ID NOs:2-8 and 10-13 polypeptide and are encoded by a nucleic acid molecule that hybridizes with a nucleic acid encoding SEQ ID NOs:2-8 and 10-13 or a complement thereof. One of skill in the art can easily determine nucleic acid sequences that encode polypeptides of the invention using readily available codon tables. As such, these nucleic acid sequences are not presented herein.

The stringency of hybridization for a nucleic acid encoding a polypeptide that is a functionally active variant is, for example, 10% formamide, 5×SSPE, 1× Denhart's solution, and 1× salmon sperm DNA (low stringency conditions). More preferable conditions are, 25% formamide, 5×SSPE, 1× Denhart's solution, and 1× salmon sperm DNA (moderate stringency conditions), and even more preferable conditions are, 50% formamide, 5×SSPE, 1× Denhart's solution, and 1× salmon sperm DNA (high stringency conditions). However, several factors influence the stringency of hybridization other than the above-described formamide concentration, and one skilled in the art can suitably select these factors to accomplish a similar stringency.

Nucleic acid molecules encoding a functionally active variant polypeptide can also be isolated by a gene amplification method such as PCR using a portion of a nucleic acid molecule DNA encoding a polypeptide shown in SEQ ID NOs:2-8 and 10-13 as the probe.

Polypeptides of the invention can also comprise those that arise as a result of the existence of multiple genes, alternative transcription events, alternative RNA splicing events, and alternative translational and postranslational events. A polypeptide can be expressed in systems, e.g., cultured cells, which result in substantially the same postranslational modifications present as when the polypeptide is expressed in a native cell, or in systems that result in the alteration or omission of postranslational modifications, e.g., glycosylation or cleavage, present when expressed in a native cell.

A polypeptide of the invention can be produced as a fusion protein that contains other non-IgE or non-IgE-derived amino acid sequences, such as amino acid linkers or signal sequences, as well as ligands useful in protein purification, such as glutathione-S-transferase, histidine tag, and staphylococcal protein A. More than one polypeptide of the invention can be present in a fusion protein. The heterologous polypeptide can be fused, for example, to the N-terminus or C-terminus of the polypeptide. A polypeptide of the invention can also comprise homologous amino acid sequences, i.e., other IgE or IgE-derived sequences.

Polynucleotides of the Invention

Polynucleotides of the invention contain less than an entire genome and can be RNA or single- or double-stranded DNA or combinations or modifications thereof. Preferably, the polynucleotides are purified free of other components, such as proteins and lipids. The polynucleotides of the invention encode the polypeptides described above, as well as fragments thereof. One of skill in the art can obtain the polynucleotide sequence of the invention using the disclosed polypeptide sequence and codon tables. Polynucleotides can contain naturally occurring polynucleotides or sequences that differ from those of any naturally occurring sequences or polynucleotides. In one embodiment of the invention, a polynucleotide of the invention is derived from a mammal, such as a human, a non-human primate, a cat, a dog, a horse, a mouse, a rat, or a swine. Polynucleotides of the invention can differ from naturally occurring nucleic acids, but still encode naturally occurring amino acids due to the degeneracy of the genetic code. Polynucleotides of the invention can also comprise other heterologous nucleotide sequences, such as sequences coding for linkers, signal sequences, heterologous signal sequences, TMR stop transfer sequences, transmembrane domains, or ligands useful in protein purification such as glutathione-S-transferase, histidine tag, and staphylococcal protein A. Polynucleotides of the invention can also comprise other homologous nucleotide sequences, i.e., other IgE or IgE-derived sequences.

An isolated polynucleotide is a nucleic acid molecule that is not immediately contiguous with 5' and 3' flanking sequences with which it is normally contiguous when present in a naturally occurring genome. Therefore, an isolated polynucleotide can be, for example, a polynucleotide that is incorporated into a vector, such as a plasmid or viral vector, a polynucleotide that is incorporated into the genome of a heterologous cell (or the genome of a homologous cell, but at a site different from that where it naturally occurs); and a polynucleotide that exists as a separate molecule such as a polynucleotide produced by PCR amplification, chemically synthesis, restriction enzyme digestion, or in vitro transcription. An isolated polynucleotide is also a nucleic acid molecule, such as a recombinant nucleic acid molecule that forms part of hybrid polynucleotide encoding additional polypeptide sequences that can be used for example, in the production of a fusion protein.

A polynucleotide can also comprise one or more expression control sequences such as promoters or enhancers, for example. A polynucleotide of the invention can be present in a vector, such as, for example, an expression vector. If desired, polynucleotides can be cloned into an expression vector comprising, for example, promoters, enhancers, or other expression control sequences that drive expression of the polynucleotides of the invention in host cells. The polynucleotides can be operably linked to the expression control sequences. An expression vector can be, for example, a plasmid, such as pBR322, pUC, or ColE1, or an adenovirus vector, such as an adenovirus Type 2 vector or Type 5 vector. Vectors suitable for use in the present invention include, for example, bacterial vectors, mammalian vectors, viral vectors (such as retroviral, adenoviral, adeno-associated viral, herpes virus, simian virus 40 (SV40), and bovine papilloma virus vectors) and baculovirus-derived vectors for use in insect cells. Polynucleotides in such vectors are preferably operably linked to a promoter, which is selected based on, e.g., the cell type in which expression is sought.

Host cells into which vectors, such as expression vectors, comprising polynucleotides of the invention can be introduced include, for example, prokaryotic cells (e.g., bacterial cells) and eukaryotic cells (e.g., yeast cells; insect cells; and mammalian cells). Such host cells are available from a number of different sources that are known to those skilled in the art, e.g., the American Type Culture Collection (ATCC), Rockville, Md. Host cells into which the polynucleotides of the invention have been introduced, as well as their progeny, even if not identical to the parental cells, due to mutations, are included in the invention.

Methods for introducing polynucleotides of the invention (e.g., vectors comprising the polynucleotides or naked polynucleotides) into cells, either transiently or stably, are well known in the art. For example, transformation methods using standard $CaCl_2$, $MgCl_2$, or RbCl methods, protoplast fusion methods or transfection of naked or encapsulated nucleic acids using calcium phosphate precipitation, microinjection, viral infection, and electroporation.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

Polynucleotides can be synthesized in the laboratory, for example, using an automatic synthesizer. An amplification method such as PCR can be used to amplify polynucleotides from either genomic DNA or cDNA encoding the polypeptides.

Antibodies of the Invention

Antibodies, such as monoclonal and polyclonal antibodies, that specifically bind to polypeptides of the invention are part of the invention. These antibodies can be made by using a polypeptide or a polypeptide fragment that contains an epitope present in a polypeptide show in SEQ ID NO:1 or SEQ ID NO:9, including, for example, SEQ ID NOs:2-8 and 10-13, as an immunogen in standard antibody production methods (see e.g., Kohler et al., Nature, 256:495, 1975; Ausubel et al. (1992) Current Protocols in Molecular Biology, John Wylie and Sons, Inc. New York, N.Y.; Harlow and Lane, Eds, (1988) Current Edition, Antibodies: A Laboratory Manual, Cold Spring Harbor Press, N.Y.).

An antibody is an intact immunoglobulin molecule, a fragment of an immunoglobulin molecule, such as Fab, Fab', (Fab')$_2$, Fv, or a single-chain antibody or fragments thereof, that specifically binds to a polypeptide of the invention (e.g., SEQ ID NOs:1-13 and fragments thereof). Antibody fragments retain some ability to selectively bind to the antigen (e.g., a polypeptide of the invention) from which they are derived, and can be made using well known methods in the art. In one embodiment of the invention, an antibody, antibody fragment or single-chain antibody comprises all such antibodies that specifically bind to a polypeptide of the invention (e.g., SEQ ID NOs:1-13 and fragments thereof) except for 15A.2 and c15A.2 (a chimeric caninized form of 15A.2).

Polypeptides of the invention comprise at least one epitope. An epitope is an antigenic determinant of a polypeptide. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span the entire polypeptide sequence, can be prepared by proteolytic cleavage. By starting with, for example, 10-mer polypeptide fragments, each fragment can be tested for the presence of epitopes recognized in, for example, an enzyme-linked immunosorbent assay (ELISA). In an ELISA assay a polypeptide, such as a 10-mer polypeptide fragment, is attached to a solid support, such as the wells of a plastic multi-well plate. A population of antibodies are labeled, added to the solid support and allowed to bind to the unlabeled antigen, under conditions where non-specific adsorption is blocked, and any unbound antibody and other proteins are washed away. Antibody binding is detected by, for example, a reaction that converts a colorless indicator reagent into a colored reaction product. Progressively smaller and overlapping fragments can then be tested from an identified 10-mer to map the epitope of interest.

Antigens that can be used in producing antibodies of the invention include polypeptides and polypeptide fragments of the invention. A polypeptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize an animal (e.g., a mouse, a rat, or a rabbit). In addition to such carriers, well known adjuvants can be administered with the antigen to facilitate induction of a strong immune response.

Polyclonal and monoclonal antibodies can be purified, for example, by binding to, and elution from, a matrix containing a polypeptide or polypeptide fragment of the invention to which the antibodies were raised. Additional methods for antibody purification and concentration are well known in the art and can be practiced with the antibodies of the invention. Anti-idiotype antibodies corresponding to polypeptides of the invention are also included in the invention, and can be produced using standard methods.

An antibody and antigen (e.g., a polypeptide or polypeptide fragment of the invention) specifically bind to each other if they bind to each other with greater affinity than to other, non-specific molecules. For example, an antibody raised against an antigen to which it binds more efficiently than to a non-specific protein can be described as specifically binding to the antigen.

In one embodiment of the invention an antibody of the invention specifically binds free mammalian IgE, binds to mammalian IgE wherein the IgE is bound to a B cell low affinity receptor (i.e., CD23 or FcεRII), does not substantially bind to IgE wherein the IgE is bound to basophils, and does not substantially bind to IgE wherein the IgE is bound to mast cells. An antibody, antibody fragment, or single-chain antibody of the invention specifically binds an IgE molecule and prevents binding of the IgE molecule to a high affinity receptor.

Monoclonal antibody 15A.2 is an example of an antibody of the invention. 15A.2 was produced by immunizing mice with affinity-purified canine IgE. See U.S. patent application Ser. No. 09/058,331, filed Apr. 9, 1998; U.S. patent application Ser. No. 09/281,760, filed Mar. 30, 1999; WO00/58365; U.S. patent application Ser. No. 09/058,332, filed Apr. 9, 1998; U.S. patent application Ser. No. 09/281,761, filed Mar. 30, 1999; WO/0058349. The epitope bound by 15A.2 is conformational and is shown in SEQ ID NO:2. 15A.2 binds to free IgE and to IgE bound to a B cell low affinity receptor. 15A.2 does not substantially bind to IgE bound to basophils and does not substantially bind to IgE bound to mast cells. Therefore, access to the epitope bound by 15A.2 is hindered by IgE binding to the high affinity receptor on mast cells. As such, 15A.2 will not crosslink IgE bound to mast cells. One embodiment of the invention comprises a purified polypeptide that specifically binds, for example, a 15A.2 monoclonal antibody. Mammalian IgE alignment with an 15A.2 epitope that is capable of specifically binding to IgE and blocking binding of IgE to a high affinity receptor is shown in FIG. 4.

Antibodies of the invention can be used, for example, to detect IgE polypeptides in a biological sample. Antibodies of the invention can be used in vitro or in vivo for immunodiagnosis. The antibodies are suited for use in, for example, immunoassays in which they are in liquid phase or bound to a solid phase carrier (e.g., a glass, polystyrene, polypropylene, polyethylene, dextran, nylon, amylase, natural and modified cellulose, polyacrylamide, agarose, or magnetite carrier). The antibodies used in such immunoassays can be detectably labeled (e.g., with an enzyme, a radioisotope, a fluorescent compound, a colloidal metal, a chemiluminescent compound, a phosphorescent compound, or a bioluminescent compound) using any of several standard methods that are well known in the art. Examples of immunoassays in which the antibodies of the invention can be used include, e.g., competitive and non-competitive immunoassays, which are carried out using either direct or indirect formats. Examples of such immunoassays include radioimmunoassays (RIA) and sandwich assays (e.g., enzyme-linked immunosorbent assays (ELISAs)). Detection of antigens using the antibodies of the invention can be done using immunoassays that are run in either forward, reverse, or simultaneous modes, including immunohistochemical assays on physiological samples. Other immunoassay formats are well known in the art, and can be used in the invention.

Antibodies of the invention can be chimeric antibodies, for example, humanized or caninized antibodies. See e.g., U.S. patent application Ser. No. 09/592,998, filed Jun. 12, 2000 (now U.S. Pat. No. 6,504,013); PCT application US01/02924, filed Jan. 30, 2001 for examples of caninized monoclonal antibody c15A.2. A humanized antibody, like a mouse-human chimeric antibody, can be prepared, for example, as follows: (1) isolate the gene encoding the antibody of the present invention from antibody-producing mouse cells; (2) replace the constant region of the H chain of the antibody with that of the human IgE; and (3) introduce into, for example, mouse myeloma J558L cells (See, Neuberger et al., Nature 314:268-270 (1985)). Alternatively, human antibodies or canine antibodies, for example, can be prepared by immunizing mice whose immune systems have been replaced with that of humans or canines with a polypeptide or polypeptide fragment of the present invention.

The invention also provides an antibody, antibody fragment, or single-chain antibody that competes with monoclonal antibody 15A.2 for binding to an IgE molecule. The binding of the antibody, antibody fragment or single-chain antibody or the monoclonal antibody 15A.2 to the IgE molecule inhibits binding of the IgE molecule to a high affinity receptor. The IgE molecule can be a mammalian IgE molecule.

The invention also provides a first antibody, antibody fragment, or single-chain antibody that competes with a second antibody, antibody fragment, or single-chain antibody for binding to an IgE molecule. The second antibody, antibody fragment, or single-chain antibody binds specifically to a polypeptide show in SEQ ID NO:1 or SEQ ID NO:9. The binding of the first or second antibody, antibody fragment, or single-chain antibody to the IgE molecule inhibits binding of the IgE molecule to a high affinity receptor. The IgE molecule can be a mammalian IgE molecule.

The invention also provides a polypeptide that competes with monoclonal antibody 15A.2 for binding to an IgE molecule. The binding of the polypeptide or the monoclonal antibody 15A.2 to the IgE molecule can inhibit binding of the IgE molecule to a high affinity receptor. The IgE molecule can be a mammalian IgE molecule.

The invention also provides a polypeptide that competes with an antibody, antibody fragment, or single-chain antibody that binds specifically to a polypeptide shown in SEQ ID NO:1 or SEQ ID NO:9 for binding to an IgE molecule. The binding of the polypeptide or antibody, antibody fragment, or single-chain antibody to the IgE molecule inhibits binding of the IgE molecule to a high affinity receptor. The IgE molecule can be a mammalian IgE molecule.

The term "competes" means that an antibody or polypeptide binds to the same or a similar antigenic determinant of IgE as a first antibody, and competes for that antigenic determinant when the first antibody and antibody or polypeptide are present in a solution and in the presence of IgE. The IgE can be either free in solution or bound to a cell, matrix or other ligand. To determine if an antibody, antibody fragment, or single-chain antibody has the same specificity as a 15A.2 monoclonal antibody or other antibody such as an antibody that binds specifically to a polypeptide show in SEQ ID NO:1 or SEQ ID NO:9, a competitive assay can be performed for binding to IgE, such as mammalian IgE. If the antibody being tested competes for binding to an IgE molecule with a 15A.2 monoclonal antibody (as shown by a decrease in binding by the 15A.2 monoclonal antibody), then the two antibodies (or polypeptides) bind to the same, or a closely related, epitope.

Still another way to determine whether an antibody or polypeptide has the specificity of a, for example, 15A.2 monoclonal antibody is to pre-incubate the antibody being tested with IgE, and then add the 15A.2 antibody to determine if its binding to IgE is inhibited. If binding by the 15A.2 monoclonal antibody is inhibited (by for example 50%, 75%, 80%, 90%, 95%, 98%, 99%, or 100%) then the antibody or polypeptide being tested has the same, or functionally equivalent, epitopic specificity as the 15A.2 antibody.

Aptamers of the Invention

An aptamer is a nucleic acid molecule (e.g., DNA or RNA or analogs thereof) that is capable of binding to a particular target molecule (e.g., a protein or polypeptide) with high affinity and specificity. See e.g., Tuerk and Gold, Science 249:505 (1990), Ellington and Szostak, Nature, 346:818 (1990).

Aptamers can bind protein targets and disrupt the interactions of the protein target with other proteins and/or disrupt catalysis by the protein targets. See e.g., Blind et al., Proc. Natl. Acad. Sci., 96:3606-3610 (1999); U.S. Pat. No. 5,756, 291; U.S. Pat. No. 5,840,867; Osborne et al., Curr. Opin. Chem. Biol. 1:5-9 (1997).

Aptamers of the invention have specific binding regions that form complexes with a polypeptide shown in SEQ ID NO:1 and/or SEQ ID NO:9 under conditions where other non-specific substances are not complexed with the aptamer. Aptamers of the invention can also complex with a protein comprising SEQ ID NO:1 and/or SEQ ID NO:9 under conditions where other non-specific substances are not complexed with the aptamer. The specificity of binding is defined in terms of comparative dissociation constants (Kd) of an aptamer for its ligand (in this case SEQ ID NO:1 and/or SEQ ID NO:9) as compared to the dissociation constant of the aptamer for other non-specific substances. Typically, the Kd of an aptamer for its ligand is about 10-fold less that the Kd for the aptamer for non-specific substances. In other embodiments, the Kd is about 50-fold, 100-fold, or 200-fold less that the Kd for the aptamer for non-specific substances. An aptamer can be, for example, 10, 20, 50, 100, 150, 200, 300, 400, or 500 nucleotides in length.

Aptamers can be identified for a specific polypeptide or protein target using for, example, selective evolution of ligands by exponential enrichment (SELEX) methods. See e.g., Wilson and Szortak, Ann. Rev. Biochem. 68:611-647 (1999); Sun, Curr. Opin. Mol. Ther. 2:100-5 (2000); U.S. Pat. No. 5,861,254; U.S. Pat. No. 5,475,096; U.S. Pat. No. 5,595, 877; U.S. Pat. No. 5,660,985; see also, U.S. Pat. No. 6,180, 348; Bock et al., Nature, 355:564-566 (1990); Conrad et al., Methods in Enzymol., 267:336-367 (1996).

Methods of Preventing IgE Binding

Polypeptides of the invention can be administered to a subject as a therapeutic to actively immunize the subject. Optionally, an antibody, antibody fragment or single-chain antibody of the invention can be administered to a subject as a therapeutic to passively immunize a subject. A subject can be, for example, a mammal such as a human, a non-human primate, a cat, a dog, a horse, a mouse, a rat, or a swine. One embodiment of the invention provides a composition for use in the treatment or prevention of allergy symptoms in a mammalian subject, which comprises an immunologically effective amount of a polypeptide of the invention (e.g., SEQ ID NO:1 or SEQ ID NO:9) or an antibody, antibody fragment, or single-chain antibody or fragment thereof of the invention and one or more pharmaceutically acceptable carriers. Treatment is the reduction, amelioration, or elimination of one or more allergy symptoms.

An immunologically effective amount is an amount sufficient to stimulate the immune system, directly or indirectly, and confer immunity against IgE-mediated diseases, such as allergies, or symptoms thereof. An effective amount is determined the severity of the disease, age, sex and weight of the patient, as well as the patient's general condition, and by other considerations known to the attending physician.

Compositions of the invention can optionally comprise pharmaceutically acceptable carriers, diluents additives, excipients and adjuvants. By the terms "pharmaceutically acceptable carriers, diluents additives, excipients and adjuvants" is meant any inert, non-toxic material that can assist in the efficient delivery of the active ingredient.

An antibody is said to be "directed against" a molecule if it is capable of specifically reacting with the molecule and specifically binding the molecule. An epitope refers to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

The invention provides methods of preventing an IgE molecule from binding to a high affinity receptor comprising contacting the IgE molecule with a molecule that specifically binds to a portion of the IgE molecule comprising SEQ ID NO:1, SEQ ID NO:9, or both SEQ ID NO:1 and SEQ ID NO:1 and SEQ ID NO:9. The molecule can be, for example, an antibody, antibody fragment, single-chain antibody, or apatmer. The contacting can occur in vivo, for example, in a mammalian subject, or in vitro.

The invention also provides compositions for use in treatment or prevention of allergy symptoms in a mammalian subject, which comprises an immunologically effective amount of a polypeptide shown in SEQ ID NO:1 or SEQ ID NO:9 or both SEQ ID NO:1 and SEQ ID NO:9 and one or more pharmaceutically acceptable carriers. Optionally, an adjuvant can also be present in the composition, or can be administered before or after the composition. Such compositions can be administered to a mammalian subject for the treatment or prevention of one or more allergy symptoms.

The invention also provides compositions for use in the treatment or prevention of one or more allergy symptoms comprising an immunologically effective amount of an antibody, antibody fragment, or single-chain antibody of the invention and one or more pharmaceutically acceptable carriers. Such compositions can be administered to a mammalian subject for the treatment or prevention of one or more allergy symptoms.

The invention additionally provides compositions for use in the treatment or prevention or one or more allergy symptoms comprising an immonolgically effective amount of a polynucleotide that encodes one or more polypeptides shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or fragments thereof and one or more pharmaceutically acceptable carriers. Such compositions can be administered to a mammalian subject for the treatment or prevention of one or more allergy symptoms.

Compositions of the invention can be used to illicit immunity to allergic reactions and symptoms. Administration of antibodies, antibody fragments, or single-chain antibodies of the invention to a subject can provide humoral immunity. This passive immunization provides substantially immediate protection. Active immunization can be achieved by administering polypeptides and/or polynucleotides and/or aptamers of the invention to a subject.

In one embodiment of the invention various polynucleotide constructs, including polynucleotides of the invention and aptamers of the invention can be used as part of a gene therapy protocol to deliver polynucleotides of the invention to a subject. For example, expression vectors can be used for in vivo transfection and expression of a polypeptide.

Allergic diseases and symptoms in a subject can be reduced and/or prevented following the generation of an immune response in the subject by immunization with polynucleotides and/or polypeptides and/or aptamers of the invention. Numerous immunotherapeutic products can be used to generate antibodies that will block the binding between IgE molecules and high affinity receptor molecules.

The injection of one or more polypeptides of the invention can result in production of anti-IgE antibodies, resulting in a reduction in e.g., allergic diseases and symptoms thereof. This effect is mediated by an inhibition of IgE binding to high affinity receptors.

Modifications can be made to a polypeptide of the invention to increase its immunogenecity. A polypeptide can be conjugated or coupled with a carrier, e.g. a Cholera toxin B chain or monoclonal antibody. The polypeptide can be precipitated with aluminum salts or cross-linked with formaldehyde or other aldehydes. The polypeptide can be mixed with a physiologically acceptable diluent such as water, phosphate buffered saline, or saline. A composition of the invention can further comprise an adjuvant. In addition to RIBI adjuvant, adjuvants such as incomplete Freund's adjuvant, aluminum phosphate, aluminum hydroxide are all well known in the art. Additional descriptions of antigenic protein-adjuvant combinations are described in WO 99/54452 and WO 99/49890.

Polypeptides, polynucleotides, antibodies, and aptamers of the invention can be delivered by numerous delivery routes, including, for example, injection, deposition, implantation, suppositories, oral ingestion, inhalation (e.g., delivery via a nasal spray), and topical administration (e.g., delivery via a skin patch).

A polynucleotide can be directly administered, for example by injection, to a subject and expressed as a protein. The DNA or RNA can be either associated with a delivery vehicle (e.g., viruses, bacteria, liposomes, and gold beads) or naked (free from association with transfection-facilitating proteins, viral particles, liposomal formulations, charged lipids and calcium phosphate precipitating). The polynucleotide can optionally include a promoter, e.g., a viral promoter. The polypeptide encoded by the polynucleotide is produced in the subject, resulting in the generation of an immune response. Methods of delivery of polynucleotides to a host cell are described in Akhtar et al., 1992, *Trends Cell Bio.*, 2, 139; *Delivery Strategies for Antisense Oligonucleotide Therapeutics*, ed. Akhtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, *ACS Symp. Ser.*, 752, 184-192. Polynucleotides can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the polynucleotide/vehicle combination is locally delivered by direct injection or by use of an infusion pump. Direct injection of the polynucleotide molecules of the invention, whether subcutaneous, intramuscular, or intradermal, can take place using standard needle and syringe methodologies, or by needle-free technologies such as those described in Conry et al., 1999, *Clin. Cancer Res.*, 5, 2330-2337 and Barry et al., International PCT Publication No. WO 99/31262. Osmotic pump (see Chun et al., 1998, *Neuroscience Letters*, 257, 135-138, D'Aldin et al., 1998, *Mol. Brain Research*, 55, 151-164, Dryden et al., 1998, *J. Endocrinol.*, 157, 169-175, Ghirnikar et al., 1998, *Neuroscience Letters*, 247, 21-24) or direct infusion (Broaddus et al., 1997, *Neurosurg. Focus*, 3, article 4) techniques can also be used. Other routes of delivery include, but are not limited to oral (tablet or pill form) and/or intrathecal delivery (Gold, 1997, *Neuroscience*, 76, 1153-1158).

A polynucleotide of the invention can also be included in the genome of a plant, so that a polypeptide of the invention is produced by the plant. The genetically-modified plant is then consumed by a subject, resulting in the ingestion of a polypeptide of the invention and the generation of an immune response. Edible plant vaccines are described in, e.g., WO 99/54452. An edible vaccine is administered orally, e.g., consuming a genetically-modified plant. The genetically-modified plant can be in the form of a plant part, extract, juice, liquid, powder, or tablet. The edible vaccine can also be administered via an intranasal route.

Attenuated viruses or bacteria can be used in the invention by genetically-modifying an attenuated virus or bacteria so that it expresses a polypeptide of the invention. This modified vector can then be delivered to a subject, resulting in the in vivo production of the polynucleotide such that an immune response is generated in the subject. Polynucleotide molecules can be inserted into microorganisms by standard methods known in the art. See e.g., U.S. Pat. No. 5,866,136 and U.S. Pat. No. 6,025,164.

The compositions and methods of the invention can be used to treat or prevent allergic diseases or symptoms in a subject at risk or suffering from allergic diseases or symptoms by stimulating an immune response in the subject by immunotherapy. Immunotherapy can comprise an initial immunization followed by additional, e.g. one, two, or three, boosters.

An immunologically effective amount of a polypeptide, antibody, or antibody fragment, or single-chain antibody of the invention is an amount that is delivered to a mammalian subject, either in a single dose or as part of a series, which is effective for treatment or prevention of one or more allergy symptoms. This amount varies depending upon the health and physical condition of the individual to be treated, the taxonomic group of individual to be treated, the capacity of the individual's immune system to synthesize antibodies, the degree of protection desired, the formulation of the vaccine, the assessment of the medical situation, and other relevant factors. It is expected that the amount will fall in a relatively broad range that can be determined through routine trials.

For example, antibodies of the invention can be administered to a subject at a dose of, for example, from about 0.05 mg to about 5 mg, followed by optional repeat (booster) doses of the same at, for example, 1 week, 2 weeks, 3 weeks, 4 weeks, two months, three months and/or a year later. Polypeptides, polynucleotides, and aptamers of the invention can be administered to a subject at a dose of about 1 µg to about 10 mg, with optional boosters given at, for example, 1 week, 2 weeks, 3 weeks, 4 weeks, two months, three months and/or a year later.

A pharmaceutically effective dose is that dose required to treat or prevent one or more allergy symptoms in a subject. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

Allergy symptoms include, but are not limited to, sinus infections, rhinitis, rash/dermatitis, headache, anaphylaxis, asthma, hives, itchy watery eyes, sternutation, cough, conjunctivitis, difficulty swallowing, nasal polyps, shortness of breath, wheezing, popping in ears, angioedema, and vomiting.

Polypeptides and antibodies of the invention can be administered to a subject by any means known in the art. The polypeptides and antibodies of the invention can be present in a pharmaceutically acceptable formulation or composition. A pharmaceutically acceptable composition or formulation comprises one or more polypeptides and/or antibodies and preferably, a pharmaceutically acceptable carrier, such as a stabilizer, buffer, and/or the like. The one or more polypeptides and/or antibodies can be administered and introduced into a subject by any standard means, with or without stabilizers, buffers, and the like, to form a pharmaceutically acceptable composition or formulation. A pharmaceutically acceptable carrier can comprise an adjuvant. Pharmaceutically acceptable formulations or compositions treat or prevent one or more allergy symptoms in a subject.

The present invention also includes pharmaceutically acceptable compositions prepared for storage or administration, which include the desired compounds in a pharmaceutically acceptable carrier, diluent, or adjuvant. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically acceptable composition or formulation is in a form suitable for administration into a cell or subject. Suitable forms, in part, depend upon the use or the route of entry, for example oral, transdermal, or by injection. Such forms should not prevent the composition or formulation from reaching a target cell or organ. For example, pharmacological compositions injected into the blood stream should be soluble. Other factors are known in the art, and include considerations such as toxicity and forms that prevent the composition or formulation from exerting its effect.

A pharmaceutically acceptable formulation of the invention can be delivered to a subject by a liposome delivery mechanism. Standard protocols for formation of liposomes can be followed. The compositions of the present invention can also be formulated and used as for example, tablets, capsules or elixirs for oral administration, suppositories for rectal administration, sterile solutions, suspensions for injectable or inhalation administration.

The pharmaceutically acceptable formulations can be locally delivered by, for example, direct injection or by use of an infusion pump. Direct injection, such as subcutaneous, intramuscular, or intradermal injection, can take place using standard needle and syringe methodologies, or by needle-free technologies such as those described in Conry et al., 1999, *Clin. Cancer Res.*, 5, 2330-2337 and Barry et al., International PCT Publication No. WO 99/31262.

Compositions of the invention can be delivered to a subject by systemic administration. Systemic administration is in vivo systemic absorption or accumulation of drugs in the blood stream followed by distribution throughout the entire body. Administration routes that can lead to systemic absorption include, without limitation: intravenous, subcutaneous, intraperitoneal, inhalation, transdermal, oral, intrapulmonary and intramuscular.

The compositions of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intradermal, intramuscular, or intrathecal injection or infusion techniques and the like.

The pharmaceutical compositions can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient or ingredients in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutically acceptable compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono-or diglycerides. In addition, fatty acids such as oleic acid find use in the preparation of injectables.

The compositions of the invention can also be administered in the form of suppositories, e.g., for rectal administration of the drugs. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

A mouse monoclonal antibody was made using native canine IgE as an immunogen using standard techniques. The resulting monoclonal antibody, 15A.2 recognizes an epitope shown in SEQ ID NO:2. The antibody binds to canine exon 3 and inhibits binding of IgE to high affinity IgE receptor on mast cells and basophils, and does not bind to canine IgE bound by high affinity IgE receptor Ph.D.-7™ Phage Display Peptide Library, Ph.D.-12™ Phage Display Peptide Library, and Ph.D.-C7C™ Phage Display Peptide Library kits were used to identify peptide ligands specific for a 15A.2 monoclonal antibody. Phage-displayed peptides that bound 15A.2 were isolated and the displayed peptides identified. The displayed peptides are shown in FIG. 1.

Example 2

The following peptide was synthesized: SVTLCPNPHIP-MCGGGK (SEQ ID NO:14). This synthetic peptide corresponds to isolate M13-48 (See Example 1 and FIG. 1). The epsilon carbon of the N-terminal K residue was biotinylated. The peptide was treated in a manner to promote reduction and cyclization of the cysteine residues to form a cyclic peptide. A serial dilution of the peptide was prepared and bound to streptavidin-coated microtiter plates (5 μg of streptavidin per well). 15A.2 was conjugated with horseradish peroxidase (HRPO) and added to the wells to detect the bound synthetic peptide (FIG. 2).

Example 3

Figure 3A:
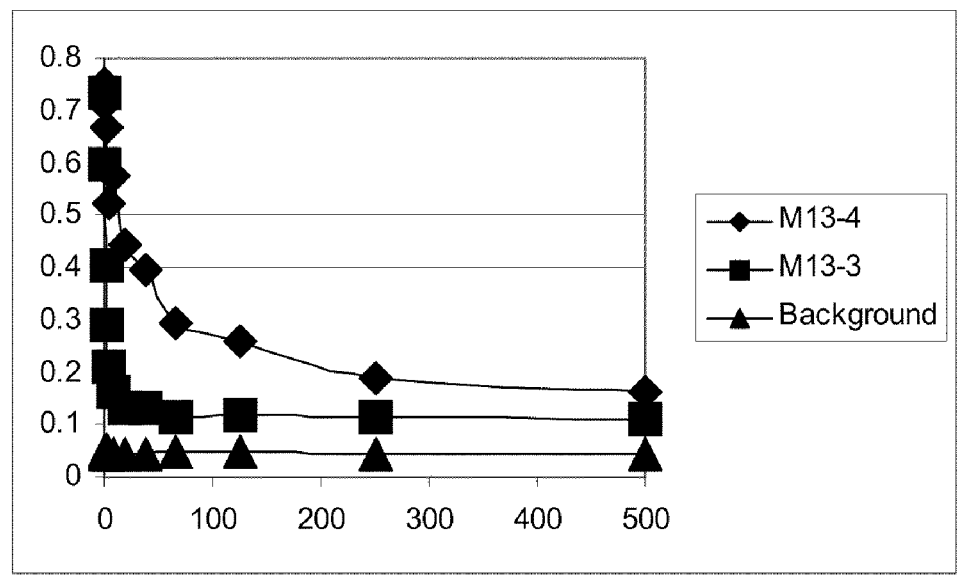
FIG. 3A-B shows phage displaying 15A.2 binding peptides competing with canine IgE for binding to monoclonal antibody 15A.2.
Figure 3B:
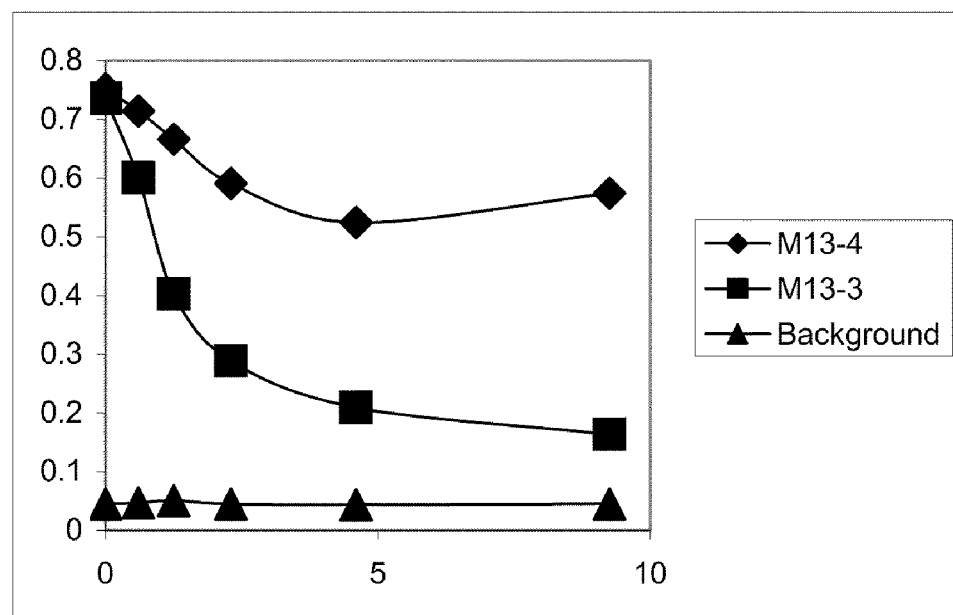

This example demonstrates the competition of phage displaying 15A.2 binding peptides with canine IgE for binding to monoclonal antibody 15A.2. 466 μl of biotinylated 15A.2 (10 μg/ml) was mixed with 466 μl of a fresh, overnight culture of phage (either 8H.8 displaying phage (8H.8 is a monoclonal antibody that is specific for canine IgE, but is not specific for SEQ ID NO:1 or SEQ ID NO:9), M13-14 phage, M13-7 phage, or no phage at all). Wells of a microtiter plate were coated with streptavidin and 100 μl of the phage/15A.2 mixture was added to each well and incubated for 2.5 hours. The microtiter plate was washed three times with standard wash buffer to remove loosely bound material. A starting concentration of 1 μg/100 μl of PBS, 0.1% TWEEN® (polysorbate), canine IgE was serially diluted. 100 μl of diluted IgE was added to each well and allowed to bind for 10 minutes. The competition reaction was stopped by washing the plates five times with wash solution. The plate was developed with HRPO-linked D9, a monoclonal antibody that binds to domain 4 of IgE. The results are shown in FIG. 3A-B.

Example 4

Neutralization of IgE by Chimeric 15A.2 Antibody

Figure 5:
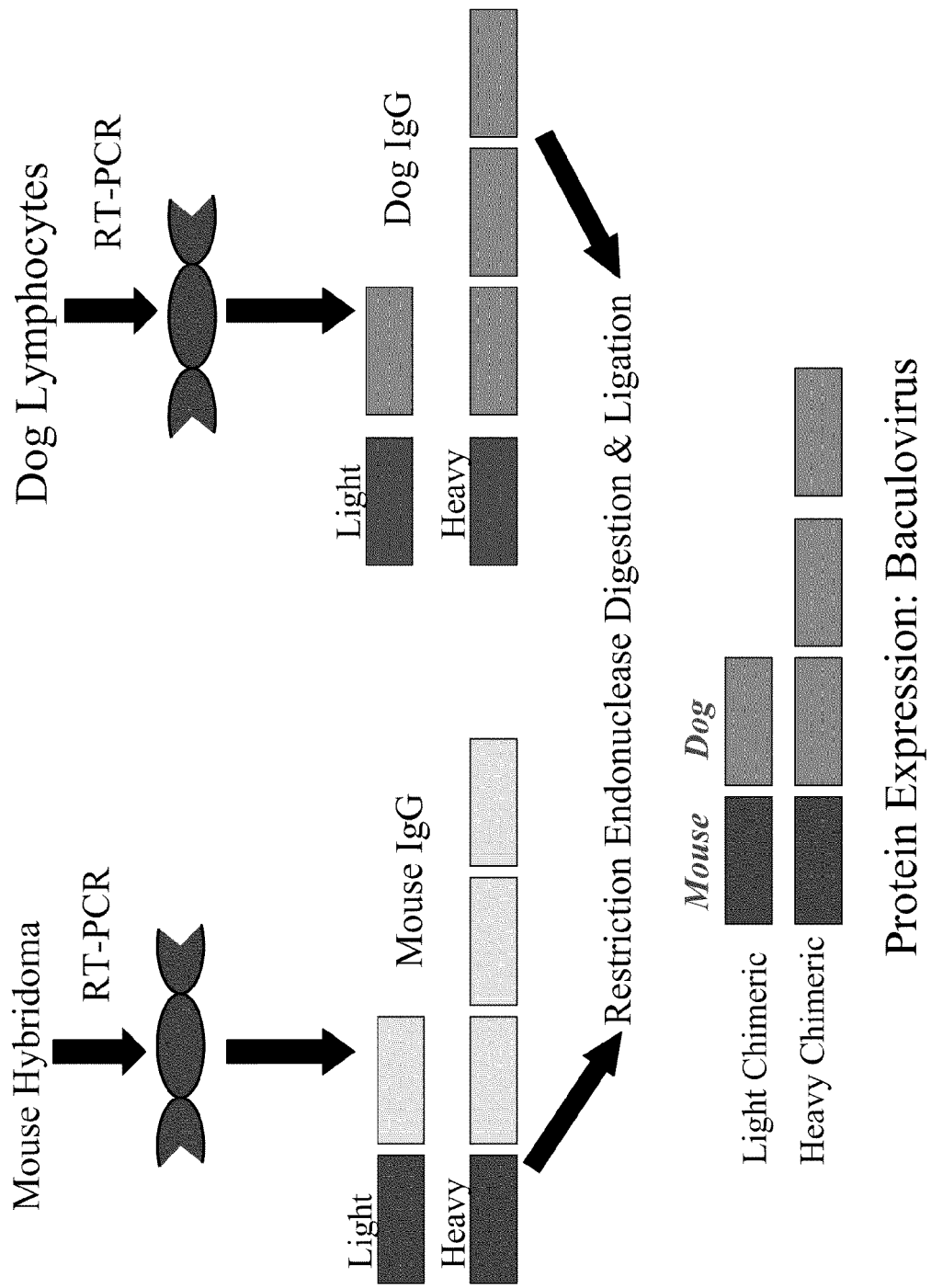
FIG. 5 depicts the construction of the chimeric c15A.2 monoclonal antibody.
Figure 6:
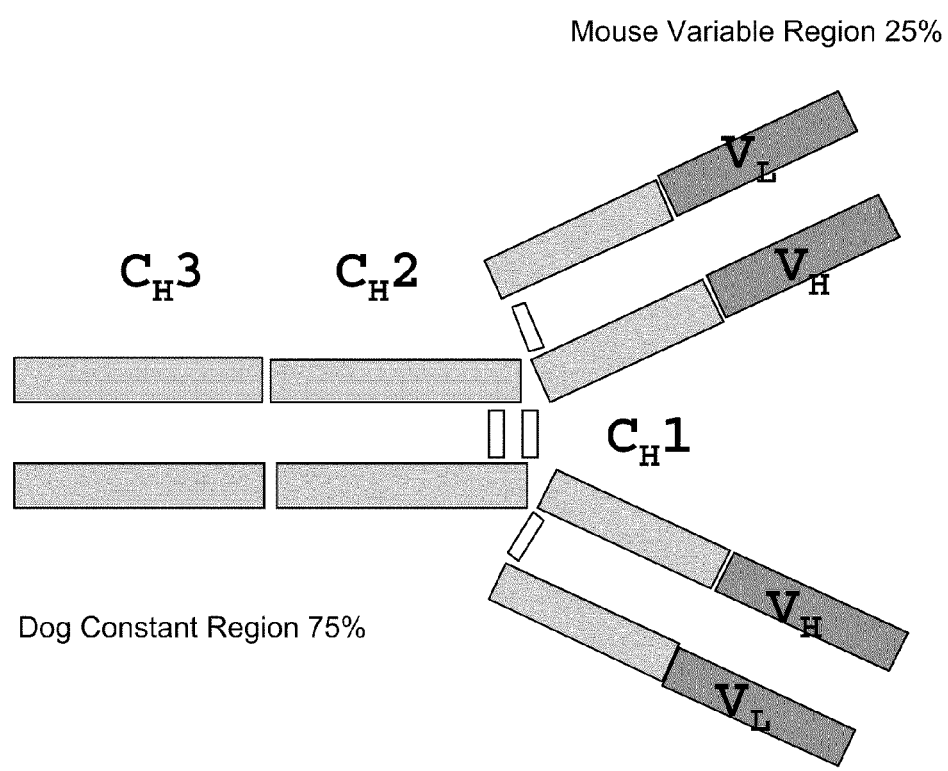
FIG. 6 depicts the structure of the chimeric c15A.2 monoclonal antibody.

A chimeric mouse/dog monoclonal antibody, c15A.2, was constructed. See FIG. 5 and FIG. 6; U.S. application Ser. No. 09/592,998, filed Jun. 12, 2000; U.S. Application Ser. No. 60/179,629, filed Feb. 1, 2000.

Figure 7:
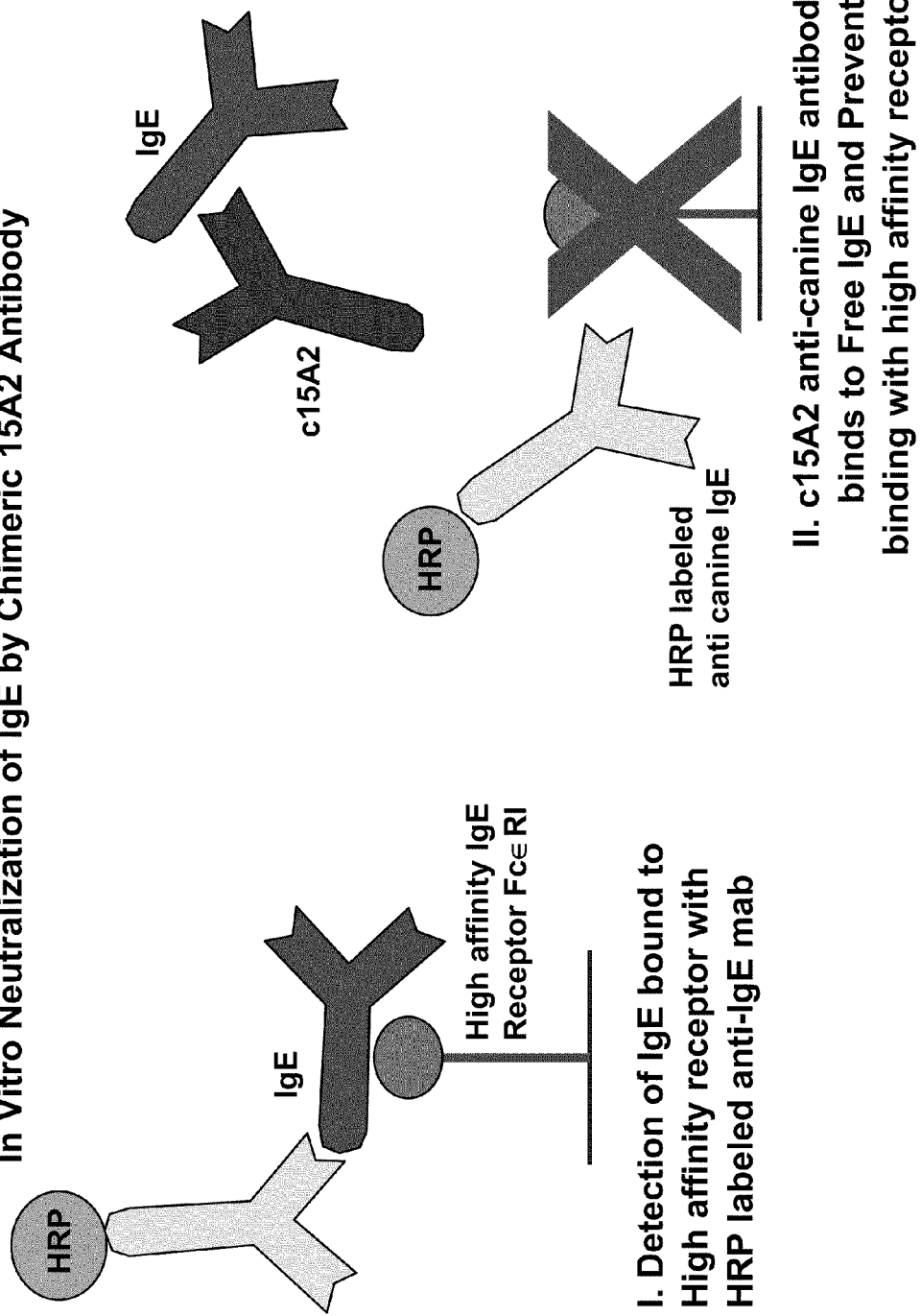
FIG. 7 demonstrates an assay for detection of IgE binding or lack of binding to immobilized high affinity IgE receptor, FcεRI.
Figure 8:
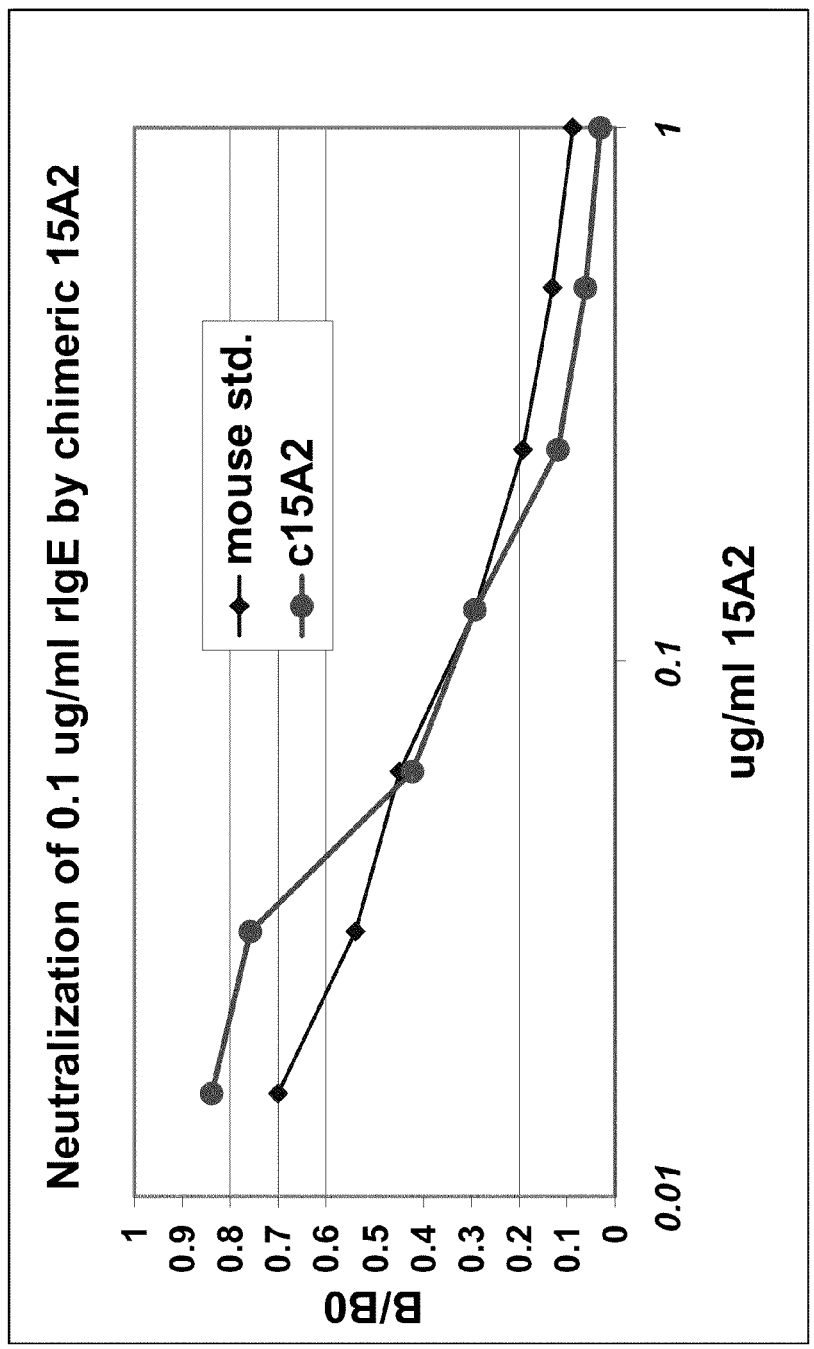
FIG. 8 shows an assay comparing a c15A2 antibody to a mouse 15A.2 antibody for the ability to inhibit IgE from binding to the high affinity IgE receptor.

High affinity IgE receptor FcεRI was immobilized onto a solid support. In the absence of c15A.2, IgE binds to the immobilized high affinity IgE receptor FcεRI. Detection of bound IgE is accomplished with a horseradish peroxidase labeled anti-IgE antibody. See FIG. 7. When IgE and c15A.2 are added to the support, c15A.2 binds free IgE and prevents it from binding to the immobilized high affinity IgE receptor FcεRI.

c15A2 antibody was compared to the mouse 15A.2 antibody for the ability to inhibit IgE from binding to the high affinity IgE receptor as described above. See FIG. 8. In this system the amount of recombinant IgE is held constant at 0.1 μg/mL. B over Bo is shown on the y-axis of FIG. 8. B over Bo is the ratio of IgE bound in the presence of inhibitor at any given point divided by the maximum binding that occurs with no inhibitor present. On the X axis of FIG. 8, the amount of antibody added to the system as an antagonist to IgE is shown. As the concentration of antibody increases from 0.01 μg/mL to 1 μg/mL the amount of IgE that is available to bind to the high affinity receptor decreases. A dose dependant decrease in IgE binding to the receptor is observed until there is essentially complete inhibition at higher antibody concentrations. Therefore, the c15A.2 antibody construct exhibited similar characteristics to the native antibody and the specificity of the chimeric antibody is retained after the antibody engineering process.

Example 5

In Vivo Neutralization of IgE by c15A.2 Antibody

Figure 9:
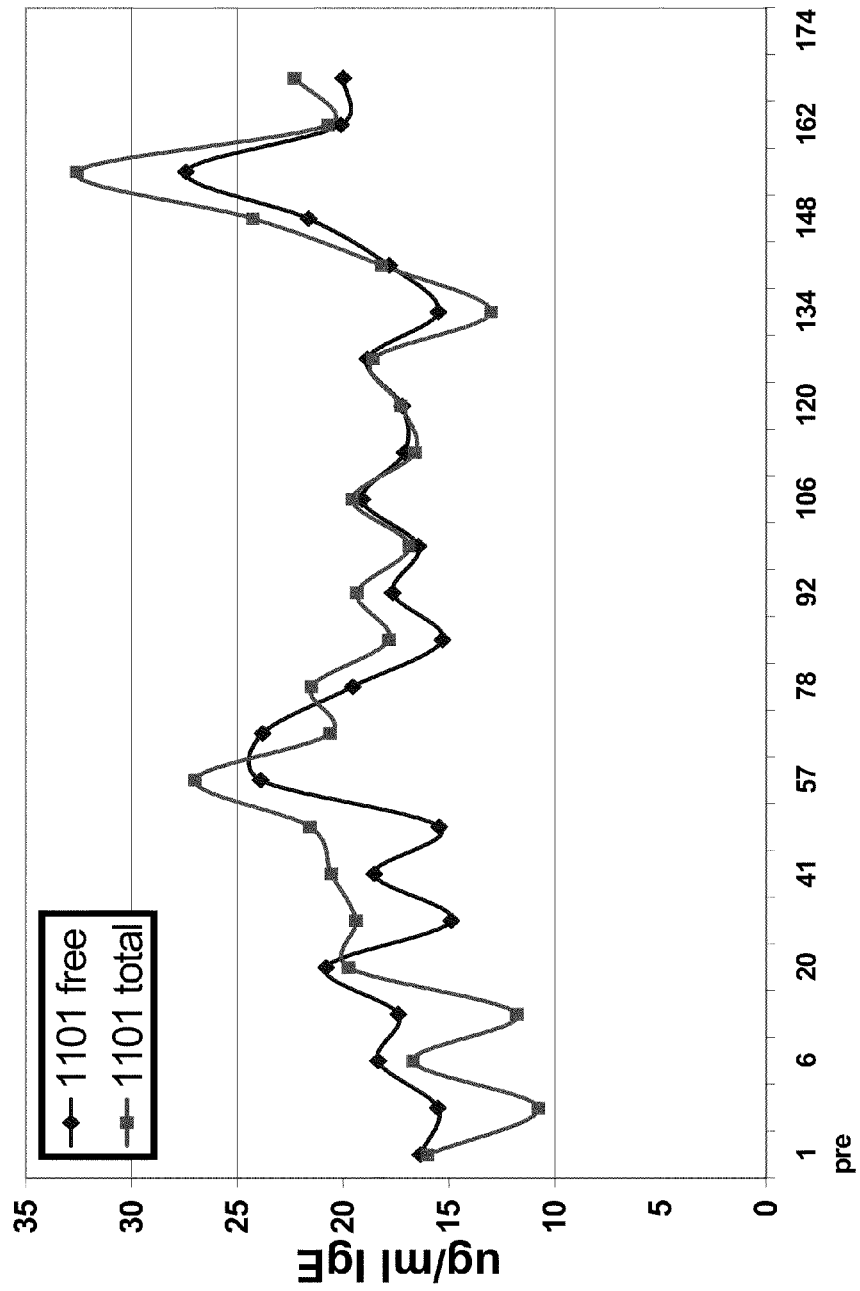
FIG. 9 shows free and total IgE levels in a representative control dog.

Dogs with ragweed positive skin test reactivity were treated with 8 consecutive doses of c15A.2 at approximately 5 day intervals. The initial and second infusion were administered at a dose of 10× free serum IgE, which was measured on day 3. Subsequent infusions were administered at a dose of 5× free serum IgE, which was measured on day 3. Free and total IgE was assayed weekly. FIG. 9 shows free and total IgE in a representative control dog over the course of the experiment. Free and total IgE parallel each other over time and IgE levels fluctuate somewhat over time in normal dogs.

Free chimeric antibody and immune complexes were assayed weekly. Ragweed sensitivity skin tests were performed pre-day zero, day 36, day 40, and day 174. Basophil IgE receptor expression was measured on day 6 and 16.

Figure 10:
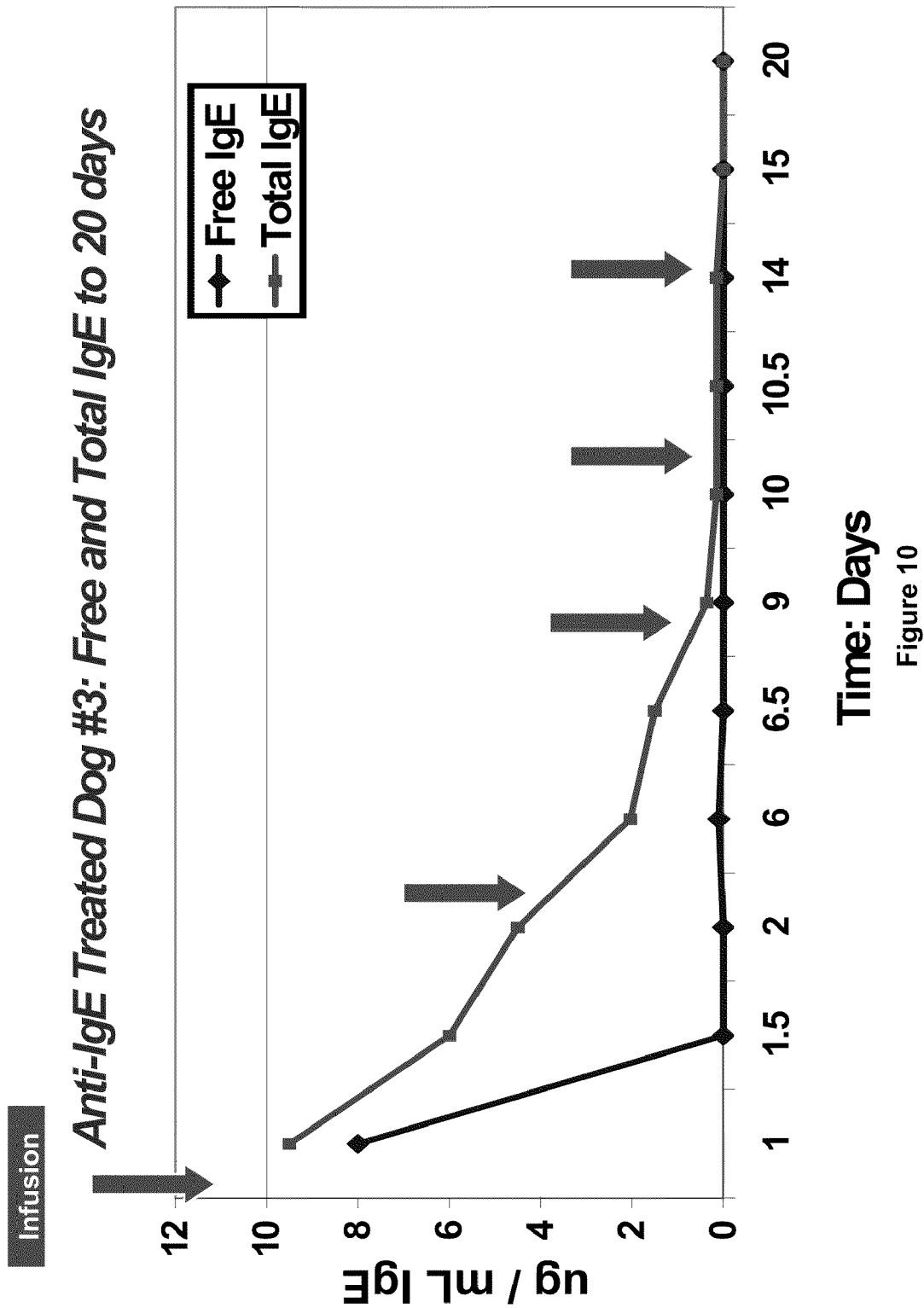
FIG. 10 shows free and total IgE levels to 20 days in a c15A.2 antibody treated dog.

The results from the free and total IgE assays to 20 days in c15A.2 antibody treated dog number 3 is shown in FIG. 10. The infusion points are shown by arrows. Immediately after infusion of the chimeric anti-IgE antibody, free IgE cannot be detected in serum. Total IgE, which is IgE that is bound by c15A.2 decreases slowly over the course of two weeks as chimeric antibody-IgE immune complexes are cleared from circulation. At approximately 14 days total IgE was undetectable.

Figure 11:
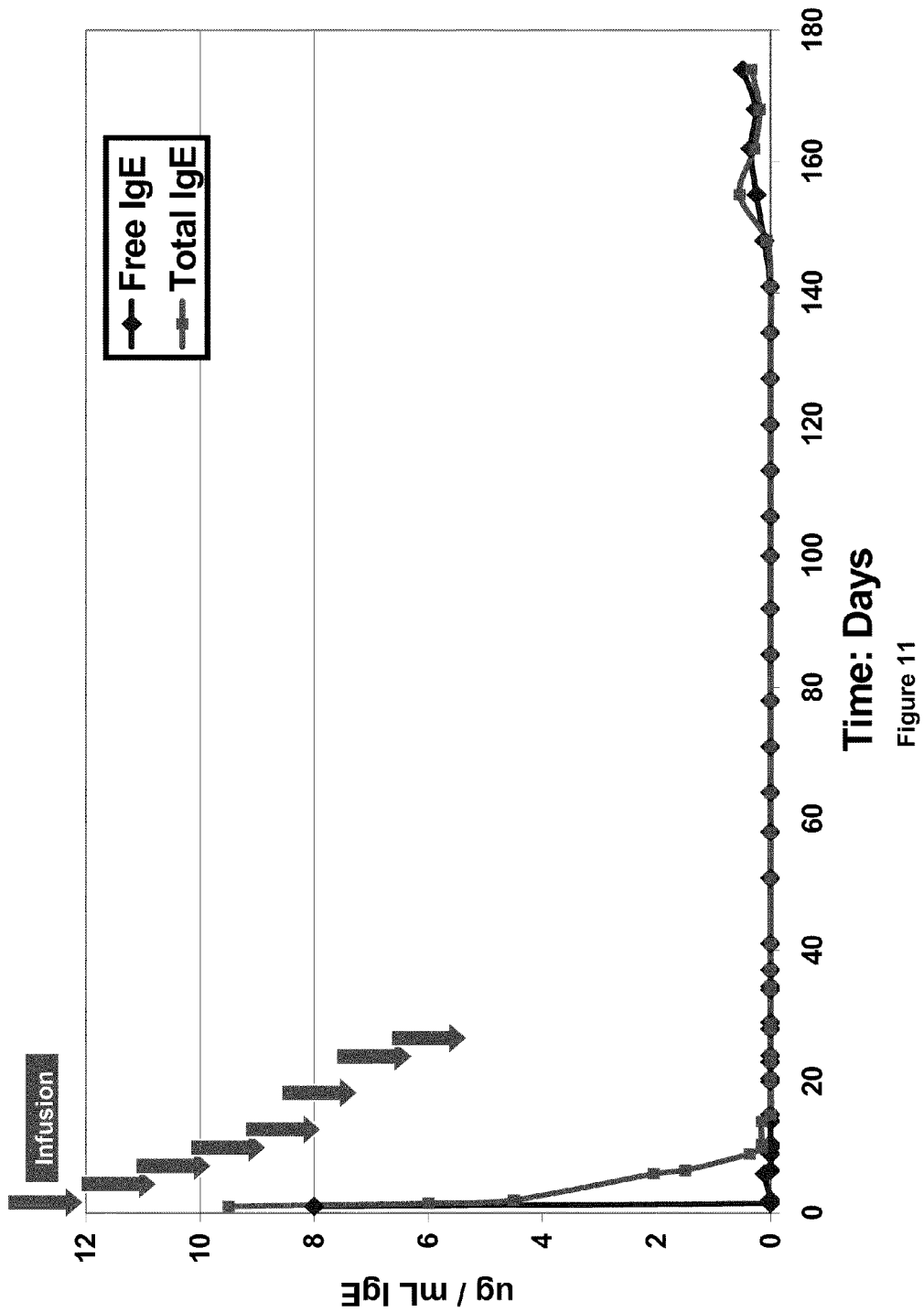
FIG. 11 shows free and total IgE levels to 174 days in a c15A.2 antibody treated dog.

The results from the free and total IgE assays through 174 days are shown in FIG. 11. Both free and serum IgE levels remained at undetectable levels long after infusion of the chimeric antibody ceased. The final infusion took place on day 33 and free and total IgE was not detected until about day 150, which was long after any chimeric antibody remained in the circulation. At about day 150 about 100 to 200 ng of IgE was detected, which was far below starting IgE levels of 8 to 10 μg per mL. This result strongly suggests that the chimeric anti-IgE antibody inhibited IgE synthesis.

Figure 12:
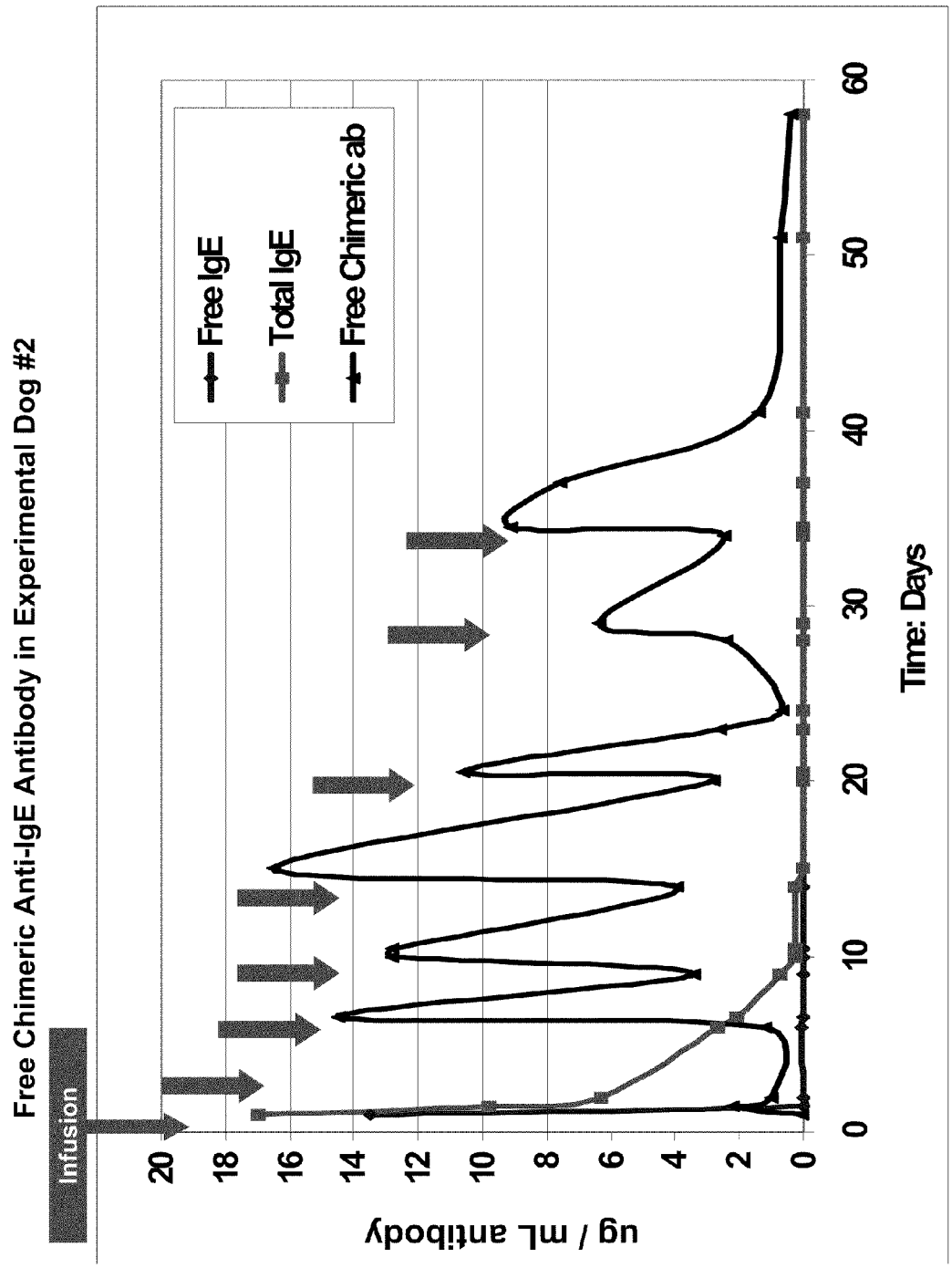
FIG. 12 shows levels of free chimeric antibody present in serum after c15A.2 infusion.

FIG. 12 shows the level of free chimeric antibody present in serum after c15A.2 infusion. This assay is performed by using a peptide mimetope of canine IgE bound to an ELISA plate. The serum is added to the plate and any chimeric antibody not bound to IgE will bind to the plate. c15A.2 is detected using a enzyme labeled polyclonal antibody specific for the Fc or canine constant domain of the chimeric antibody. After the initial infusion, low but detectable levels of chimeric antibodies can be measured. Beginning after the third infusion which took place on day 9 a spike of chimeric antibody is seen after each infusion and then the level of the chimeric antibody decreases as it is cleared. This clearance is related to the half-life of the molecule and not because of immune complex clearance of the molecule associated with IgE. After approximately 2 months after the initial infusion there is no longer any detectable chimeric antibody present.

Figure 13:
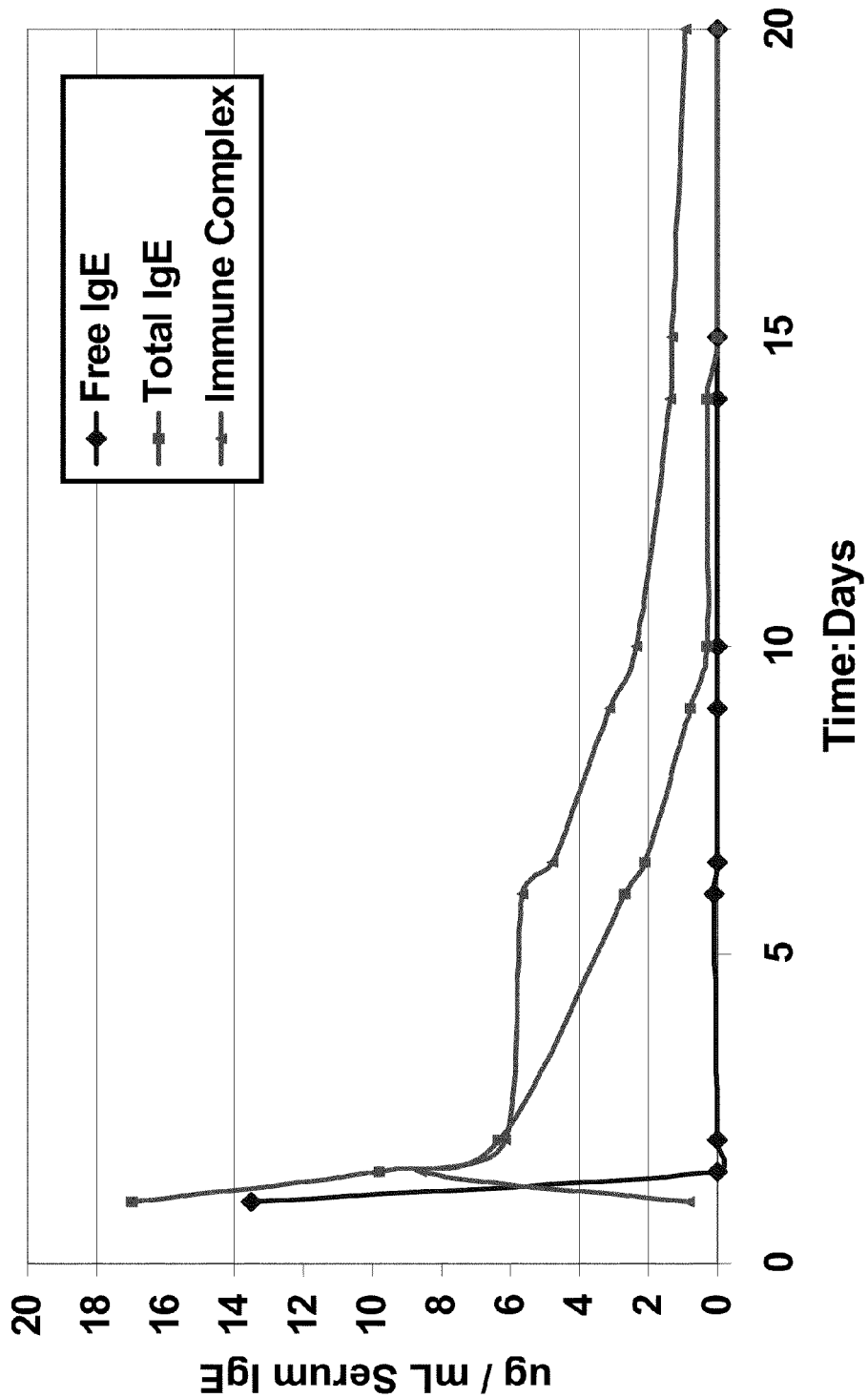
FIG. 13 demonstrates clearance of IgE-chimeric antibody immune complexes as measured directly by ELISA.

To confirm that the decrease of total IgE reflected the formation and clearance of IgE-chimeric antibody immune complexes immune were measured directly by ELISA. See FIG. 13. In this assay complexed IgE was captured using a domain 4 specific anti-IgE monoclonal antibody. The presence of the chimeric antibody, which was bound to IgE in domain 3 of IgE, was detected using an enzyme labeled polyclonal anti-canine Fc specific antibody. Total IgE levels parallel the direct measurement of chimeric antibody-IgE immune complexes.

Figure 14:
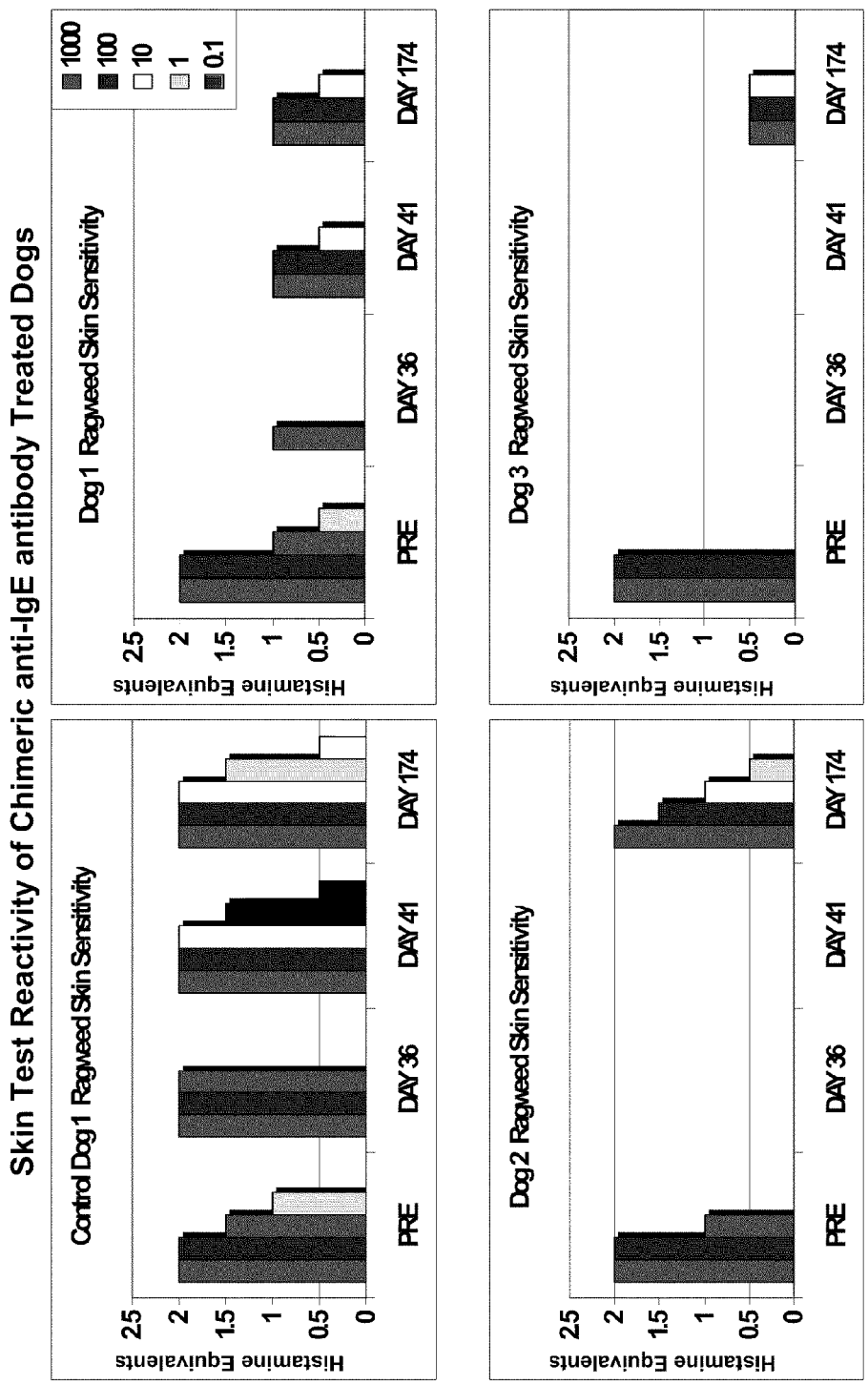
FIG. 14 shows skin test response to ragweed allergen for three experimental dogs and one control dog.

FIG. 14 shows the skin test response to ragweed allergen for three experimental dogs and one control dog. Each panel depicts 4 skin tests that were performed. There is a pre-experimental skin test followed by skin tests performed on day 36, day 41, and day 174. For each test there is a titration of ragweed allergen from 1000 protein nitrogen units to 0.1 protein nitrogen units. If the response to ragweed allergen was equivalent to the histamine control it was graded a 1 plus. In the top left panel the skin tests for the untreated dog are shown. The skin test sensitivity in this dog actually increased over the course of the experiment. For the experimentally treated dogs in the lower panels there was no detectable response to ragweed allergen at days 36 and days 41 at any dilution. In the skin test performed 6 months after the initial infusion there was skin test reactivity to ragweed that approached the pre-experimental response in dog 2 shown in the lower left panel while in dog 3 shown in the lower right panel the response remained below the pre-experimental level. In this case the 0.5 rating given indicates that there was some infusion of the evans blue dye that was used in the testing protocol but there was no swelling at the site of injection. The same can be said for dog 1 which is shown in the top right panel. The rating given was primarily due to the infusion of dye and not because of swelling at the site of injection. In this dog the skin response was lowered but not eliminated after infusion of the chimeric antibody. It is possible that the skin mast cells were not completely disarmed of IgE or it is possible that there may have been some non-specific response at the site of injection due to the testing procedure.

This example demonstrates that passive immunization of dogs with c15A.2 eliminates skin test reactivity in ragweed sensitized dogs. The example also shows that c15A.2 can bind serum IgE, prevent IgE-receptor binding, prevent mast cell degranulation, reduce IgE receptor expression on basophils and mast cells and down-regulate IgE synthesis in vivo. Passive immunization with c15A.2 eliminated free and total serum IgE levels for about 6 months. Skin test sensitivity to ragweed allergen was eliminated. The capacity to synthesize new IgE was eliminated in treated dogs for about 6 months. Additionally, IgE receptor expression was down-regulated on circulating basophils.

We claim:

1. An isolated antibody, antibody binding fragment, or single-chain antibody that specifically binds to an isolated polypeptide consisting of an amino acid sequence set forth in SEQ ID NO: 13, 15, 16, 17, 18, 19, or 20.

2. The isolated antibody of claim 1, wherein the antibody is a monoclonal antibody or a polyclonal antibody.

3. The isolated antibody binding fragment of claim 1, wherein the fragment is a Fab, Fab', (Fab')$_2$, or Fv fragment.

4. The isolated antibody, antibody binding fragment, or single-chain antibody of claim 1, wherein the isolated antibody, antibody binding fragment or single-chain antibody specifically binds free mammalian IgE, binds to mammalian IgE wherein the IgE is bound to a B cell low affinity receptor, does not substantially bind to IgE wherein the IgE is bound to basophils, and does not substantially bind to IgE wherein the IgE is bound to mast cells.

5. The isolated antibody, antibody binding fragment, or single-chain antibody of claim 4, wherein the low affinity receptor is CD23 or FcεRII.

6. The isolated antibody, antibody fragment, or single-chain antibody of claim 1, wherein the isolated antibody, antibody fragment, or single-chain antibody specifically binds an IgE molecule and prevents binding of the IgE molecule to a high affinity receptor.

7. The isolated antibody, antibody fragment, or single-chain antibody of claim 1, wherein the isolated antibody, antibody fragment, or single-chain antibody is bound to a solid phase carrier.

8. The isolated antibody, antibody fragment, or single-chain antibody of claim 1, wherein the isolated antibody, antibody fragment, or single-chain antibody is labeled.

9. The isolated antibody, antibody fragment, or single-chain antibody of claim 1, wherein the isolated antibody, antibody fragment, or single-chain antibody is chimeric.

* * * * *

```
                        SEQUENCE LISTING

<160> NUMBER OF SEQ ID NOS: 20

<210> SEQ ID NO 1
<211> LENGTH: 17
<212> TYPE: PRT
<213> ORGANISM: Artificial
<220> FEATURE:
<223> OTHER INFORMATION: Isolated polypeptide that binds to IgE.
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 1

Xaa Cys Xaa Val Xaa His Pro Xaa Xaa Pro Xaa Xaa Xaa Xaa Arg Ser
1               5                   10                  15

Xaa

<210> SEQ ID NO 2
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 2
```

```
Tyr Cys Arg Val Thr His Pro His Leu Pro Lys Asp Ile Val Arg Ser
1               5                   10                  15

Ile

<210> SEQ ID NO 3
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 3

Gln Cys Arg Val Thr His Pro His Leu Pro Arg Ala Leu Met Arg Ser
1               5                   10                  15

Thr

<210> SEQ ID NO 4
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 4

Gln Cys Arg Val Thr His Pro His Leu Pro Arg Ala Leu Val Arg Ser
1               5                   10                  15

Thr

<210> SEQ ID NO 5
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 5

Gln Cys Lys Val Thr His Pro Asp Leu Pro Leu Val Ile Val Arg Ser
1               5                   10                  15

Ile

<210> SEQ ID NO 6
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 6

Tyr Cys Asn Val Thr His Pro Asp Leu Pro Lys Pro Ile Leu Arg Ser
1               5                   10                  15

Ile

<210> SEQ ID NO 7
<211> LENGTH: 15
<212> TYPE: PRT
<213> ORGANISM: Artificial
<220> FEATURE:
<223> OTHER INFORMATION: Isolated polypeptide that binds to IgE.

<400> SEQUENCE: 7

Gln Cys Ile Val Asp His Pro Asp Phe Pro Ile Val Arg Ser Ile
1               5                   10                  15

<210> SEQ ID NO 8
```

<211> LENGTH: 16
<212> TYPE: PRT
<213> ORGANISM: Artificial
<220> FEATURE:
<223> OTHER INFORMATION: Isolated polypeptide that binds to IgE.

<400> SEQUENCE: 8

Arg Cys Thr Val Ser His Pro Asp Leu Pro Arg Glu Trp Arg Ser Ile
1 5 10 15

<210> SEQ ID NO 9
<211> LENGTH: 9
<212> TYPE: PRT
<213> ORGANISM: Artificial
<220> FEATURE:
<223> OTHER INFORMATION: Isolated polypeptide that binds to IgE.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 9

Cys Xaa Xaa Pro His Xaa Xaa Xaa Cys
1 5

<210> SEQ ID NO 10
<211> LENGTH: 9
<212> TYPE: PRT
<213> ORGANISM: Artificial
<220> FEATURE:
<223> OTHER INFORMATION: Isolated polypeptide that binds to IgE.
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Cys His Pro His Leu Pro Lys Xaa Cys
1 5

<210> SEQ ID NO 11
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 11

Cys His Pro His Leu Pro Lys Ser Cys
1 5

<210> SEQ ID NO 12
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 12

Cys His Pro His Leu Pro Lys Arg Cys
1 5

<210> SEQ ID NO 13
<211> LENGTH: 12
<212> TYPE: PRT
<213> ORGANISM: Artificial

```
<220> FEATURE:
<223> OTHER INFORMATION: Isolated polypeptide that binds to IgE.

<400> SEQUENCE: 13

Val Thr Leu Cys Pro Asn Pro His Ile Pro Met Cys
1               5                   10

<210> SEQ ID NO 14
<211> LENGTH: 17
<212> TYPE: PRT
<213> ORGANISM: Artificial
<220> FEATURE:
<223> OTHER INFORMATION: Isolated polypeptide that binds to IgE.

<400> SEQUENCE: 14

Ser Val Thr Leu Cys Pro Asn Pro His Ile Pro Met Cys Gly Gly Gly
1               5                   10                  15

Lys

<210> SEQ ID NO 15
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 15

Cys Ser Asn Pro His Val Thr His Cys
1               5

<210> SEQ ID NO 16
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 16

Cys Ser His Pro His Leu Thr His Cys
1               5

<210> SEQ ID NO 17
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 17

Cys Ser Asn Pro His Ile Thr Gln Cys
1               5

<210> SEQ ID NO 18
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 18

Cys Met Asn Pro His Ile Thr His Cys
1               5

<210> SEQ ID NO 19
<211> LENGTH: 9
<212> TYPE: PRT
<213> ORGANISM: Artificial
```

```
<220> FEATURE:
<223> OTHER INFORMATION: Isolated polypeptide that binds to IgE.

<400> SEQUENCE: 19

Cys Thr Asn Pro His Asn Pro Tyr Cys
1               5

<210> SEQ ID NO 20
<211> LENGTH: 9
<212> TYPE: PRT
<213> ORGANISM: Artificial
<220> FEATURE:
<223> OTHER INFORMATION: Isolated polypeptide that binds to IgE.

<400> SEQUENCE: 20

Cys Pro Asn Pro His Asn Pro Tyr Cys
1               5
```